United States Patent
Brozek et al.

(10) Patent No.: US 11,676,269 B2
(45) Date of Patent: Jun. 13, 2023

(54) AUTOMATED PATTERN RECOGNITION AND SCORING METHOD OF HISTOLOGICAL IMAGES

(71) Applicant: GENFIT, Loos (FR)

(72) Inventors: John Brozek, Saint-Amand-les-Eaux (FR); Nathalie Degallaix, Ervillers (FR); Benoit Noel, Gondecourt (FR); Elton Rexhepaj, Antibes (FR)

(73) Assignee: GENFIT, Loos (FR)

( * ) Notice: Subject to any disclaimer, the term of this patent is extended or adjusted under 35 U.S.C. 154(b) by 78 days.

(21) Appl. No.: 16/757,752

(22) PCT Filed: Oct. 19, 2018

(86) PCT No.: PCT/EP2018/078711
§ 371 (c)(1),
(2) Date: Apr. 20, 2020

(87) PCT Pub. No.: WO2019/077108
PCT Pub. Date: Apr. 25, 2019

(65) Prior Publication Data
US 2021/0192722 A1    Jun. 24, 2021

(30) Foreign Application Priority Data

Oct. 20, 2017 (EP) .................. 17197623
Apr. 9, 2018 (EP) .................. 18166425

(51) Int. Cl.
*G06K 9/00* (2022.01)
*G06T 7/00* (2017.01)
*G16H 10/40* (2018.01)
*G16H 30/20* (2018.01)
*G16H 50/30* (2018.01)
*G16H 50/70* (2018.01)
*G16H 50/20* (2018.01)
*G16H 30/40* (2018.01)
(Continued)

(52) U.S. Cl.
CPC ............. *G06T 7/0012* (2013.01); *G06N 3/04* (2013.01); *G06N 3/08* (2013.01); *G16H 10/40* (2018.01); *G16H 30/20* (2018.01); *G16H 30/40* (2018.01); *G16H 50/20* (2018.01); *G16H 50/30* (2018.01); *G16H 50/70* (2018.01); *G06T 2207/10056* (2013.01); *G06T 2207/20081* (2013.01); *G06T 2207/30024* (2013.01); *G06T 2207/30056* (2013.01)

(58) Field of Classification Search
None
See application file for complete search history.

(56) References Cited

U.S. PATENT DOCUMENTS

| | | |
|---|---|---|
| 2015/0339816 A1 | 11/2015 | Yu et al. |
| 2017/0032090 A1 | 2/2017 | Kamen et al. |
| 2017/0261584 A1 | 9/2017 | James et al. |

OTHER PUBLICATIONS

Mishra ("structure-based assessment of cancerous mitochondria using deep networks" IEEE, 2016, pp. 545-548) (Year: 2016).*

(Continued)

*Primary Examiner* — Wei Wen Yang
(74) *Attorney, Agent, or Firm* — McDermott Will & Emery LLP

(57) ABSTRACT

The present invention relates to a novel automated pattern recognition and scoring method of histological images.

10 Claims, 10 Drawing Sheets

(51) Int. Cl.
   *G06N 3/04* (2023.01)
   *G06N 3/08* (2023.01)

(56) References Cited

OTHER PUBLICATIONS

Goodman Z. D. ("Grading and staging systems for inflammation and fibrosis in chronic liver diseases", Journal of Hepatology 47 (2007), pp. 598-607). (Year: 2007).*

Aliper et al., Deep Learning Applications for Predicting Pharmacological Properties of Drugs and Drug Repurposing Using Transcriptomic Data. Mol Pharm. Jul. 5, 2016;13(7):2524-30. Epub Jun. 8, 2016.

Bril et al., Management of Nonalcoholic Fatty Liver Disease in Patients With Type 2 Diabetes: A Call to Action. Diabetes Care. Mar. 2017;40(3):419-430.

Goceri et al., Quantification of liver fat: A comprehensive review. Comput Biol Med. Apr. 2016 1;71:174-89. Epub Feb. 27, 2016.

Meng et al., Liver Fibrosis Classification Based on Transfer Learning and FCNet for Ultrasound Images. IEEE Access. Mar. 30, 2017;5:5804-10.

Oseini et al., Therapies in non-alcoholic steatohepatitis (NASH). Liver Int. Jan. 2017;37 Suppl l(Suppl 1):97-103.

Yasaka et al., Liver Fibrosis: Deep Convolutional Neural Network for Staging by Using Gadoxetic Acid-enhanced Hepatobiliary Phase MR Images. Radiology. Apr. 2018;287(1):146-155. Epub Dec. 14, 2017.

* cited by examiner

AUTOMATED PATTERN RECOGNITION AND SCORING METHOD OF HISTOLOGICAL IMAGES

FIELD OF THE INVENTION

The present invention relates to an automated pattern recognition and scoring method of histological images.

BACKGROUND OF THE INVENTION

The prevalence of Non Alcoholic Steatohepatitis (NASH) is rapidly growing and represents a major public health issue knowing that NASH drives progressive fibrosis accumulation ultimately leading to cirrhosis and hepatocellular carcinoma (HCC).

While Non-alcoholic fatty liver disease (NAFLD) may be diagnosed by detecting the presence of fat accumulation into the liver using ultrasound techniques, NASH and NASH-associated liver fibrosis can only today be diagnosed by histological examination of a liver biopsy. Histological scoring/staging systems have been developed for assessing NAFLD activity level and fibrosis stage and estimating the risk of evolution to clinical liver outcomes. The NALFD-Activity-Score (NAS) has been developed for assessing the activity of the disease.

The NAS is the sum of the biopsy's individual scores for steatosis (0 to 3), lobular inflammation (0 to 2), hepatocellular ballooning (0 to 2), or is the sum of unweighted individual biopsy's individual scores.

According to Kleiner et al., (Hepatology, 2005; 41:1313-21)(Kleiner et al, 2005), NAS is the sum of three histological scores made from liver biopsy slices:

Steatosis score: 0: <5%; 1: 5-33%; 2: 34-66% and 3: >66%

Lobular Inflammation score (foci/x20 field): 0: none; 1: <2; 2: 2-4 and 3>4

Ballooning degeneration score: 0: none; 1: few; 2: many.

Using this scoring system a patient with NASH has NAS≥3 and at least 1 point in steatosis, at least 1 point in lobular inflammation and at least 1 point in hepatocyte ballooning. A patient is considered as having an Active-NASH when NAS≥4 with at least 1 point in steatosis, at least 1 point in inflammation and at least 1 point in hepatocyte ballooning.

Localization and extent of fibrosis at histological exam signs the severity (advancement) of the disease and the NASH-CRN has developed a dedicated fibrosis staging system (Kleiner et al., Hepatology, 2005; 41:1313-21).

| | |
|---|---|
| Perisinusoidal or periportal fibrosis | 1 |
| Mild perisinusoidal fibrosis (zone 3) | 1a |
| Moderate perisinusoidal fibrosis (zone 3) | 1b |
| Portal/periportal fibrosis | 1c |
| Perisinusoidal and portal/periportal fibrosis | 2 |
| Bridging fibrosis | 3 |
| Cirrhosis | 4 |

Using this fibrosis staging system, patient with no or minimal fibrosis (F=0-1) are generally not considered at risk of cirrhosis, HCC or liver death. Patients with significant (F=2) and moderate fibrosis (F=3) are at increasing risk of developing cirrhosis, liver failure, HCC and liver death. Patient with compensated cirrhosis have severe fibrosis (F=4) and are at high risk of liver failure (decompensated cirrhosis), HCC and liver death.

Derived from these widely accepted two scoring and staging systems, special attention has been recently paid on the Activity Index (AI) which can be defined as the sum of the lobular inflammation score and the hepatocyte ballooning scores. In addition Munteanu et al., Aliment Pharmacol Ther., 2016, 44(8):877-89, (Munteanu et al, 2016), have proposed SAF signature to report separately scores of Steatosis, disease Activity and Fibrosis. The steatosis score (S) assesses the quantities of large or medium-sized lipid droplets, with the exception of foamy microvesicles, and rates them from 0 to 3 (S0: <5%; S1: 5-33%, mild; S2: 34-66%, moderate; S3: >66%, marked). Activity grade (A, from 0 to 4) is the unweighted addition of hepatocyte ballooning (0-2) and lobular inflammation (0-2). Cases with A0 (A=0) had no activity; A1 (A=1) had mild activity; A2 (A=2) moderate activity; A3 (A=3) severe activity and A4 (A=4) had very severe activity. Fibrosis stage (F) was assessed using the score described by Kleiner as follows: stage 0 (F0)=none; stage 1 (F1)=1a or 1b perisinusoidal zone 3 or 1c portal fibrosis; stage 2 (F2)=perisinusoidal and periportal fibrosis without bridging; stage 3 (F3)=bridging fibrosis and stage 4 (F4)=cirrhosis.

The Brunt system was proposed primarily as a method for grading the severity of NASH and was not intended to be applied to cases that did not meet minimal criteria for steatohepatitis. The grading of steatohepatitis into mild, moderate and severe was based on an overall impression of the severity of steatosis, inflammation and ballooning, but most of the weight was given to ballooning (Brunt et al, 1999).

TABLE 1

Comparison of the essential elements of NAFLD/NASH grading and staging systems (Kleiner & Makhlouf, 2016).

| Numerical Grade or Stage | Brunt System | NASH CRN System | SAF System |
|---|---|---|---|
| | | Fibrosis Stage | |
| 0 | None | None | None |
| 1 | Zone 3 perisinusoidal fibrosis only | Perisinusoidal or periportal fibrosis; 3 substages defined | Perisinusoidal or periportal fibrosis; |
| 2 | Zone 3 perisinusoidal fibrosis and periportal fibrosis | Perisinusoidal and periportal fibrosis | Perisinusoidal and periportal fibrosis |
| 3 | Bridging fibrosis | Bridging fibrosis | Bridging fibrosis |
| 4 | Cirrhosis | Cirrhosis | Cirrhosis |

TABLE 1-continued

Comparison of the essential elements of NAFLD/NASH grading
and staging systems (Kleiner & Makhlouf, 2016).

| Numerical Grade or Stage | Brunt System | NASH CRN System | SAF System |
|---|---|---|---|
| | | Ballooning Grade | |
| 0 | None | None | Only normal hepatocytes |
| 1 | Mild, zone 3 | Few | Few: Clusters of hepatocytes with rounded shape and reticulated cytoplasm |
| 2 | Prominent, zone 3 | Many | Many: Enlarged hepatocytes (≥2× normal) |
| 3 | Marked, zone 3 | | |
| | | Lobular Inflammation Grade | |
| 0 | No foci | No foci | No foci |
| 1 | 1-2 foci per 20× field | <2 foci per 20× field | <2 foci per 20× field |
| 2 | 2-4 foci per 20× field | 2-4 foci per 20× field | >2 foci per 20× field |
| 3 | >4 foci per 20× field | >4 foci per 20× field | |
| | | Portal Inflammation Grade | |
| 0 | None | None | |
| 1 | Mild | Mild | |
| 2 | Moderate | More than mild | |
| 3 | Severe | | |
| | | Steatosis Grade | |
| 0 | None | <5% | <5% |
| 1 | <33% | 5% to 33% | 5% to 33% |
| 2 | 33% to 66% | 33% to 67% | 33% to 67% |
| 3 | >66% | >67% | >67% |

Pathology is a field of science which deals with laboratory examinations of samples of tissue for diagnostic, research, or other purposes. Pathologists, as well others working in medical or biological research, examine human, animal, floral, or other tissue to assess disease state or understand biological features. In one aspect of pathology, a tissue is biopsied from a patient for analysis and fixed on a glass slide to be viewed under a light microscope. However, such form of tissue assessment is sensitive for various reasons. For example, some of such disadvantages include subjectivity and low throughput. Another problem is that a high-quality diagnosis often requires analyzing multiple samples which is challenging with a single reader. Manual readers faced with many similar samples can also experience fatigue, adding to the inconsistency of the readings.

Several studies with the attempt to quantify observer variability in the assessment of the histological features, conclude to moderate-to-substantial concordance for grade of fibrosis. In addition, hepatocyte Inflammation and ballooning did not have a good concordance among pathologists leading to an interobserver agreement of 63% on the overall pathologic diagnosis (Younossi et al, 1998). A review analysis of the prevalence of NASH in a fairly homogeneous group of patients (morbidly obese patients submitted to bariatric surgery), concluded that the prevalence of NASH based on histopathological analysis of surgical biopsies obtained at the time of surgery varied from 24 to 98% (Machado et al, 2006).

Pathologist scores are based on interpretation of micro/macro histological patterns in the biopsy sections. Current standard for scoring these clinical parameters remains the manual interpretation and scoring of liver biopsy sections by a pathologist or trained histologist. Manual scoring beside being tedious (e.g. ballooning) is known to have moderated inter-observer agreement (steatosis: κ (coefficient of concordance)=0.6, inflammation: κ=0.5, ballooning: Λ=0.7, fibrosis: κ=0.5) (Bedossa, 2014), due primarily to subjectivity in interpretation of histological patterns.

This bias is further enhanced when considering each parameter individually:

I) Hepatocyte Ballooning: For such a non-frequent event, due to non-exhaustive screening, certain cells can be missed. A subjective assessment is also made on cell size used frequently to discriminate pre-ballooned (small cells) from fully degenerated ballooned hepatocytes (large cells).

II) Hepatic or Hepatocyte Lobular Inflammation: Subjectivity due to HPFs (High Power Field) selection makes the scoring process difficult to reproduce and exposed to a potential bias.

III) Liver Fibrosis: Assessment of hepatic fibrosis is also challenging due to 1) impact of histopathological factors on quantification of collagen proportion area (CPA) and 2) human subjective interpretation for fibrosis staging (moderate inter-observer agreement (Bedossa, 2014). CPA quantification requires methods to be robust to staining variation (due to histology and imaging essentially) as well as to exclude non-pathological staining of collagen (vascular regions).

IV) Steatosis: Visual estimation of the proportion of hepatocytes containing intracellular vacuoles of fat and grading of steatosis into broad brackets of severity: grade 0 (normal)=up to 5% of cells affected, grade 1 (mild)=5-33% of cells affected, grade 2 (moderate)=34-66% of cells affected, and grade 3 (severe)=67% of cells affected are rather subjective, there is considerable inter- and intra-individual variation in steatosis grading at histopathology.

Moreover, fully automated methods are crucially needed to address current accuracy, reproducibility and throughput issues. After the spread of whole slide imaging (WSI) systems for clinical and research applications, development of machine learning applications applied to histopathological data has been a very active area of research in the recent years (LeCun et al, 2015). Deep-Learning (DL) pattern recognition algorithms have recently shown to be able to capture accurately both micro and macro tissue patterns, furthermore mimicking the diagnostic workflow of the pathologist. Using such technologies, histological patterns can be automatically predicted and reproducibility of NASH diagnosis and hepatic fibrosis scoring can be improved. In addition, recognition of NASH specific fibrosis histological patterns would allow a more accurate quantification of collagen morphology (Septa) and proportionate area (CPA).

SUMMARY OF THE INVENTION

To fully automate NASH histological interpretation, the inventors established an integrated, automated data management and analysis pipeline for the assessment of NASH disease activity, NASH fibrosis score, and hepatic fibrosis. They developed a robust stain normalization method to compensate for low to important intra and inter-cohort dye intensity variations. The inventors also investigated the use of DL and morphometric analysis through three unique fully automated machine learning applications to automate NASH scoring (inflammation, ballooning and fibrosis). Steatosis quantification using image analysis methods was also further included in the analysis to complete the automated process of NAFLD diagnosis and NASH scoring. The steatosis quantification method may be a DL method.

Given the different pathological and histological nature of each clinical parameter, the inventors have conducted a development process that was channeled into individual analysis pipelines:
  I. preprocess (Fields Of Views (FOVs) extraction, tissue segmentation, normalization).
  II. predict NASH pathological micro/macro pattern DL (Inflammatory, ballooned cells/hepatic fibrosis FOV type) and quantify steatosis area.
  III. data aggregation to the biopsy level.

Generalization properties of quantification pipelines for each NASH clinical component were assessed using independent cohorts for development, testing and validation. The final goal was to translate micro/macro predictions and quantifications (CPA/septa morphology) into clinically relevant information and to validate against the reference pathologist annotations.

Accordingly, the invention provides a method for robust automated pattern recognition and scoring method of immunochemistry images from liver biopsy.

These methods are based on Deep Learning and morphometry analysis through three unique fully automated machine learning applications to automate critical NASH individual parameters scoring (inflammation, ballooning and fibrosis). The methods may also be completed with a fourth fully automated application to automate steatosis quantification.

In the methods of the present invention, hepatocyte ballooning (HB) is assessed by using DL to predict pathologically relevant cellular patterns (i.e. ballooned hepatocytes, cell size). In a second step, these predictions may be aggregated at liver biopsy sample level.

In the methods of the present invention, lobular inflammation (LI) is assessed by using DL to predict pathologically relevant cellular patterns (i.e. inflammatory cells). In a second step, these predictions may be aggregated at liver biopsy sample level.

In the methods of the present invention, fibrosis is assessed by using DL to predict pathologically relevant liver fibrotic areas that may further be confirmed, in particular by the following CPA and fibrosis septa morphometry quantification. Fibrosis scoring may allow the clinical prognostic of fibrosis, which is the prognostic of the risk of liver fibrosis evolution to cirrhosis and liver outcomes of a NAFLD or NASH patient based on the robust scoring of liver fibrosis by the automated reading and scoring method of the invention.

In the methods of the present invention, steatosis (S) assessment may be an automated process in particular by using DL model to predict pathologically relevant cellular structures.

Such pattern may be the percentage of fatty hepatocytes containing lipid vacuoles or the area of steatosis (AOS)).

The area of steatosis is vacuole type structure.

In a particular embodiment the vacuole size is at least the size of a nucleus.

In a particular embodiment steatosis is assessed by an automated measurement of area of steatosis.

In a second step, these predictions may be aggregated at liver biopsy sample level.

For all machine learning applications, each DL model properties were critically designed to produce objective, accurate and reproducible results.

Accordingly, in a particular embodiment, the detection and quantification of hepatocyte ballooning in a subject is based on pattern recognition and scoring: HB=0, no hepatocyte ballooning, HB=1, moderate hepatocyte ballooning and HB=2, severe hepatocyte ballooning (Kleiner & Makhlouf, 2016).

In a particular embodiment, the detection and quantification of lobular inflammation in a subject is based on pattern recognition and scoring: LI=0, no lobular inflammation, LI>0, lobular inflammation and grading: LI=1 mild lobular inflammation, LI=2, moderate lobular inflammation and LI=3, severe lobular inflammation (Kleiner & Makhlouf, 2016).

In a further embodiment, the invention also provides a method for the determination and staging of the NASH activity index (AI), by the addition of individual scores of hepatocyte ballooning and lobular inflammation: AI=0 or 1, no NASH; AI>1 with at least HB=1 and LI=1.

In another embodiment, the invention allows the clinical diagnosis of NAFLD in healthy subjects or patients, based on the determination of the steatosis score in a liver biopsy and a minimal steatosis score of 1.

In another embodiment, the invention allows the clinical diagnosis of NASH in a subject, in particular in NAFLD patients, based on the determination of the activity index in a liver biopsy of a NAFLD patient: AI≥2 with at least HB=1 and LI=1.

In another embodiment, the detection and quantification of liver fibrosis in a subject is based on pattern recognition and scoring in liver biopsy: F=0, no fibrosis, F>0, detection of fibrosis and grading: F=1, minimal fibrosis, F=2, significant fibrosis, F=3, moderate fibrosis and F=4, severe fibrosis In a particular embodiment, the detection and quantification of liver steatosis in a subject is based on pattern recognition and scoring in liver biopsy: S=0, less than 5% steatosis; S=1, 6%-33% steatosis; S=2, 34%-66% steatosis; and S=3, greater than 66% steatosis (Kleiner & Makhlouf, 2016).

In a further particular embodiment, the characterization of micro-steatosis and macro-steatosis in a subject is based on pattern recognition, cell size and morphology analysis, and scoring in liver biopsy.

In a further embodiment, the localization and disposition of specific histological patterns relative to portal vein, sinusoids, lobular vein, or other substructures, may provide precious complementary information on liver pathology.

In a particular embodiment, the analysis of the histological profile can be fully automated. In another embodiment, quantification of histological NASH parameters can be automated. In a further embodiment, quantification of histological NASH parameters can be automated and integrated in a bioimage analysis software (in particular, QuPath platform).

According to a further object, the invention relates to a method for the classification of a subject as being potential receiver (to be treated, or TBT) or non-receiver (not to be treated, or NTBT) of a treatment for NAFLD, NASH or liver fibrosis, based on the reliable detection and quantification, thanks to the automated method presented herein, of Activity Index and Fibrosis in NAFLD patients and differential analysis between TBT and NTBT patients as defined below.

Through another aspect, the invention also allows the clinical prognosis of fibrosis, which is the prognostic of the risk of liver fibrosis evolution to cirrhosis and liver outcomes of a NAFLD or NASH patient based on fibrosis DL model and hepatic fibrosis morphometric model application on histological slides of liver biopsies.

The invention also provides a method for monitoring the evolution of NAFLD activity, NASH activity and/or liver fibrosis stage based on pattern recognition and scoring with DL models of histological slides of liver biopsies of subjects and differential analysis with biopsies collected in the past in the same subject. Automated steatosis scoring may further be included in the method The invention also provides a method for determining the efficiency of a treatment of NAFLD, NASH or liver fibrosis in a subject based on hepatocyte ballooning, lobular inflammation, fibrosis DL models and hepatic fibrosis morphometric model application on immunohitological slides of liver biopsies by differential analysis between pattern and scores in liver biopsy of a subject and another biopsy collected in the same subject in the past. Automated steatosis scoring may further be included in the method.

The invention further provides a method for predicting the response of a subject (prediction of changes in NAFLD, NASH activity and liver fibrosis stage) to a specific treatment (responder subject) based on hepatocyte ballooning, lobular inflammation, fibrosis DL models and hepatic fibrosis morphometric model application on immunohistological slides of liver biopsies and comparison between responders and non responders. Automated steatosis scoring may further be included in the method.

Overview of computational pathology pipeline from the reception of physical glass slide till the prediction of automated NASH and hepatic scores.

Phase I: Whole slide imaging (WSI). Slides are scanned with a glass slide scanner and stored following the DICOM recommendations, large multi-resolution multi-planar images to facilitate storage, viewing and analysis.

Phase II: Preprocessing of WSI. Slide representation at 5× is used to automatically find imaging artifacts (air bubbles, dust, coverslip debris) and tissue processing artifacts (tissue folding, tissue debris).

Phase III: Extraction of biomedical relevant images from WSI. Images representing either micro-patterns (cells) and macro-patterns(tissue regions) are extracted to be analyzed.

Phase IV: NASH and hepatic fibrosis automated scoring. Prediction models are initially trained on micro-patterns (ballooning and inflammation) and macro-patterns (NASH fibrosis, hepatic fibrosis). These models are then applied to individual micro and macro patterns images to predict for each biopsy glass slide: number of ballooned hepatocytes, number of inflammatory cells, NASH fibrosis patterns, hepatic fibrosis collagen proportionate area and hepatic fibrosis morphology index (for each macro-pattern). Micro and macro pattern quantification are then transformed into a ballooning score, inflammation score, fibrosis score, hepatic collagen proportionate area and morphology index.

Figure 1:
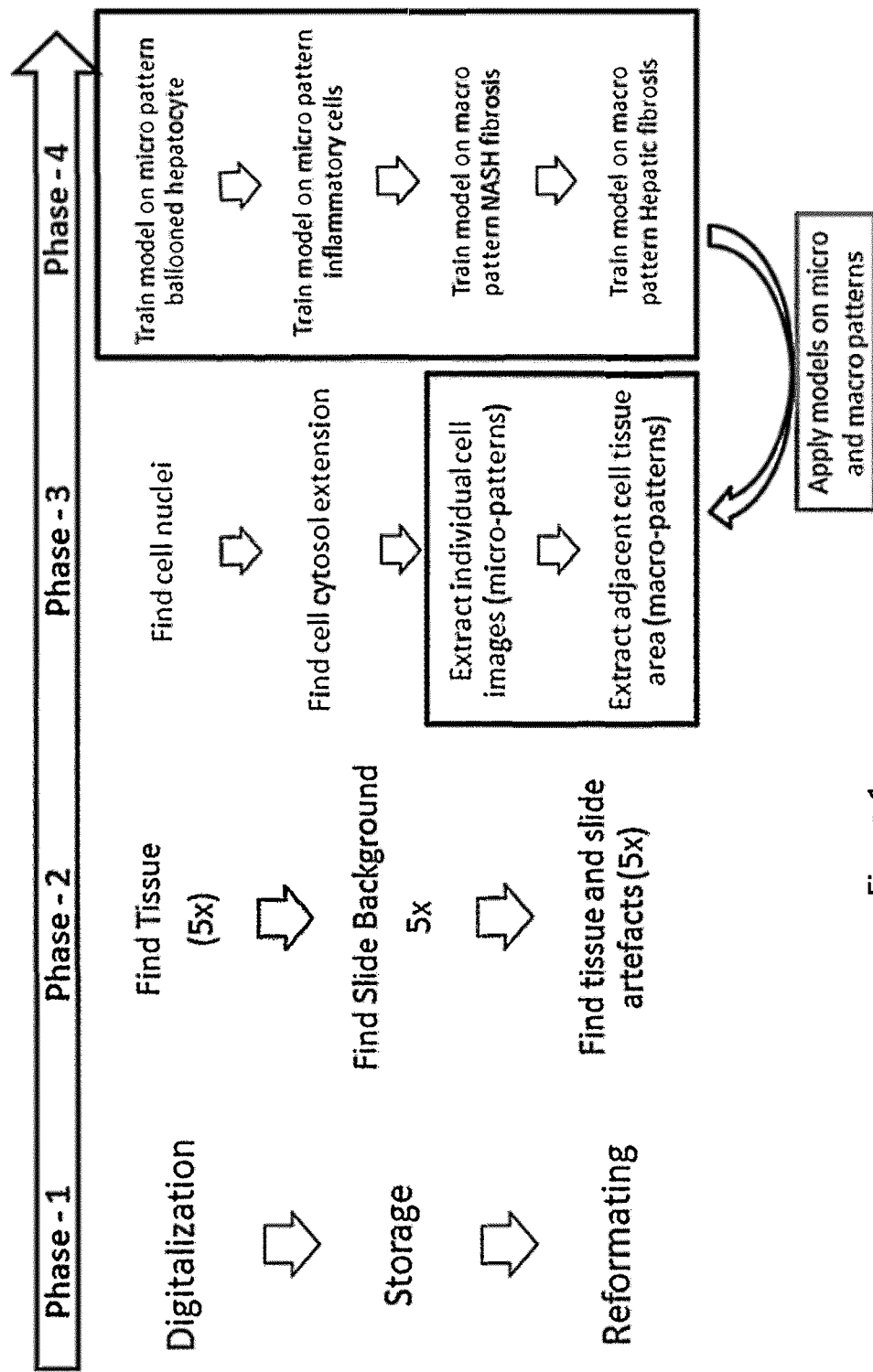
FIG. 1: Schematic overview of the protocol for pattern recognition and scoring method development.
Figure 2:
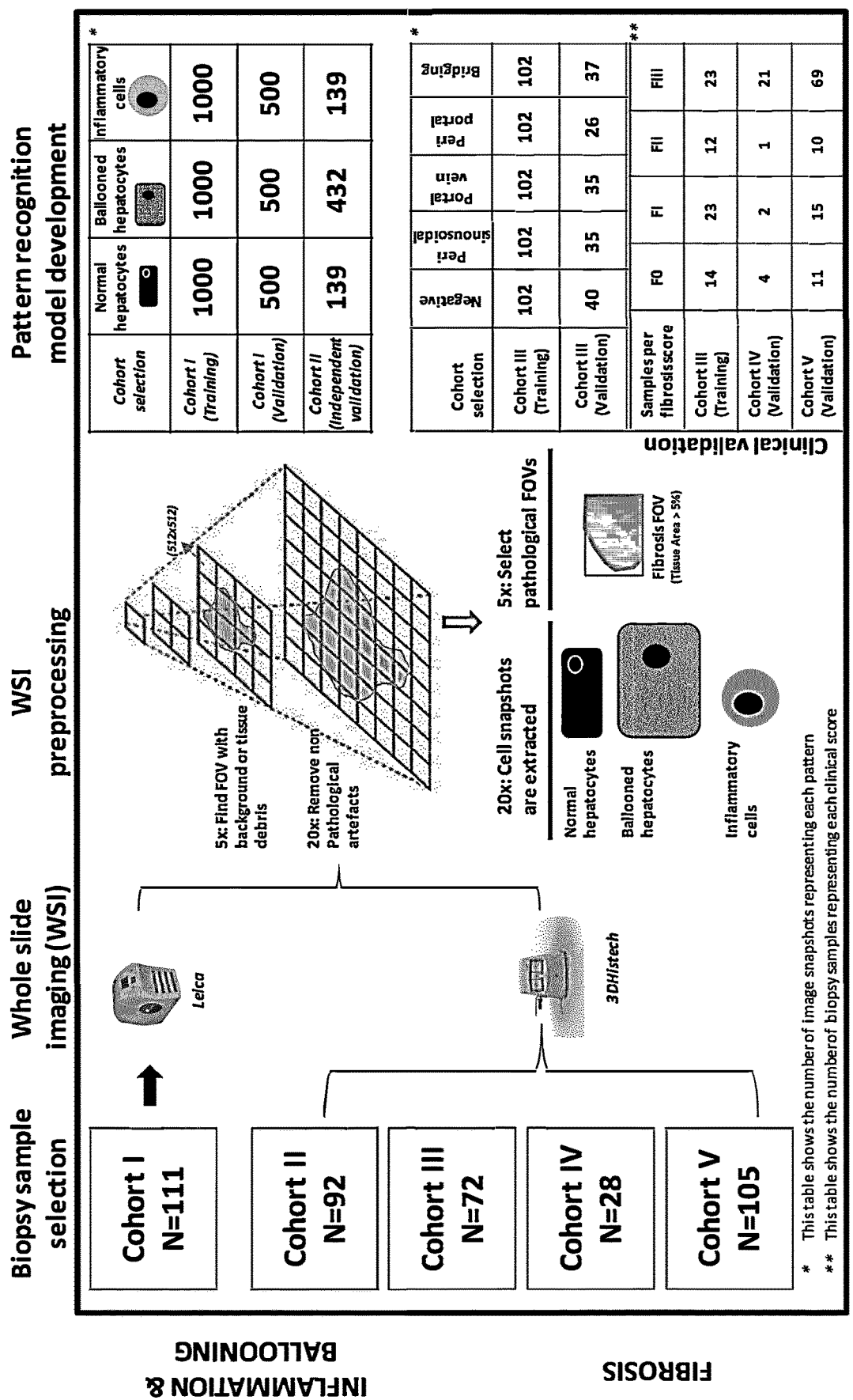

FIG. 2: Breakdown of the patient samples and image data used to generate the deep-learning model for inflammation, ballooning, fibrosis and hepatic fibrosis morphometry analysis.

Figure 3:
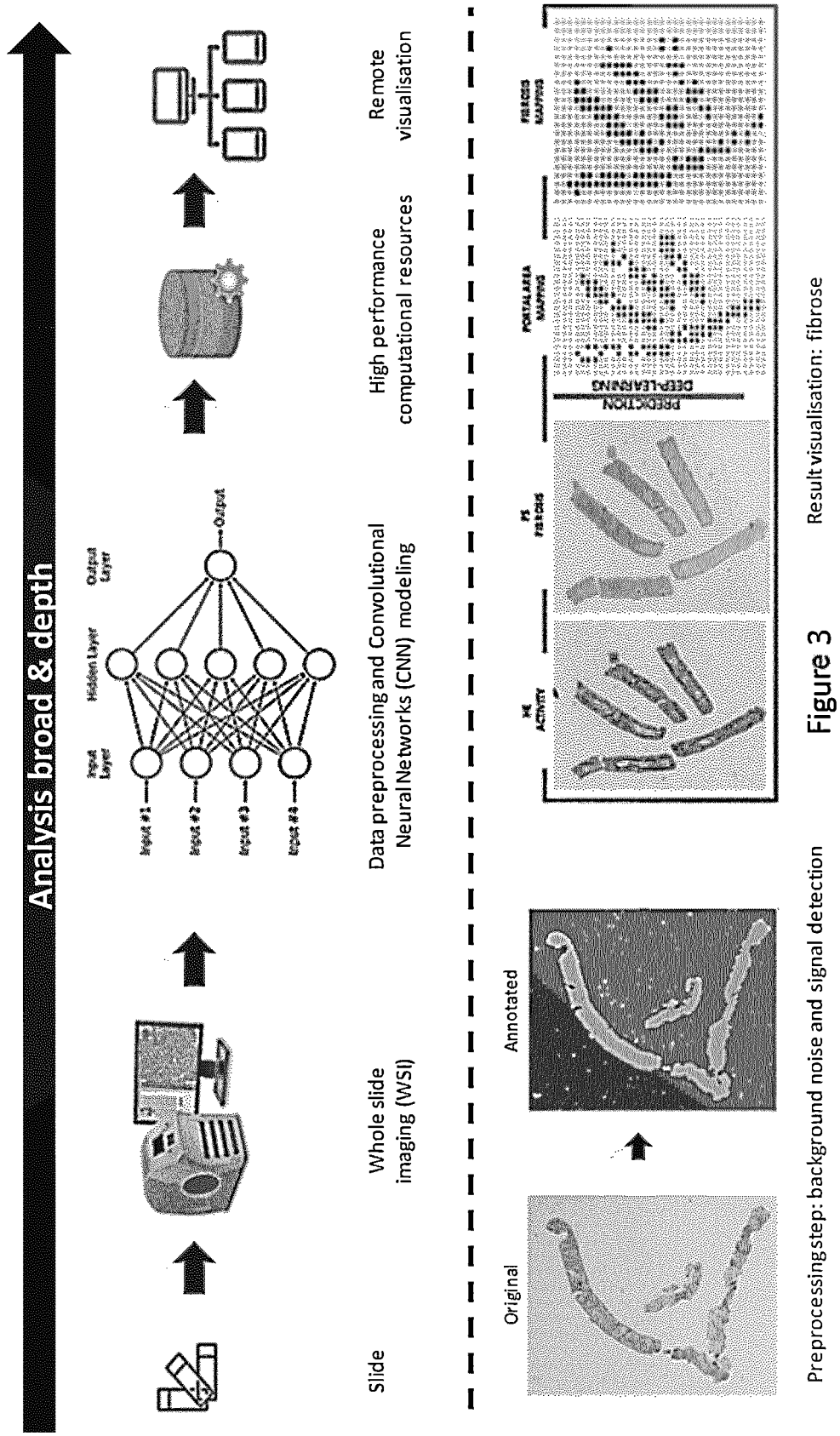

FIG. 3: Overview of the in-house developed computational pathology pipeline, covering the whole-slide imaging (WSI) data management analysis and visualization.

Figure 4:
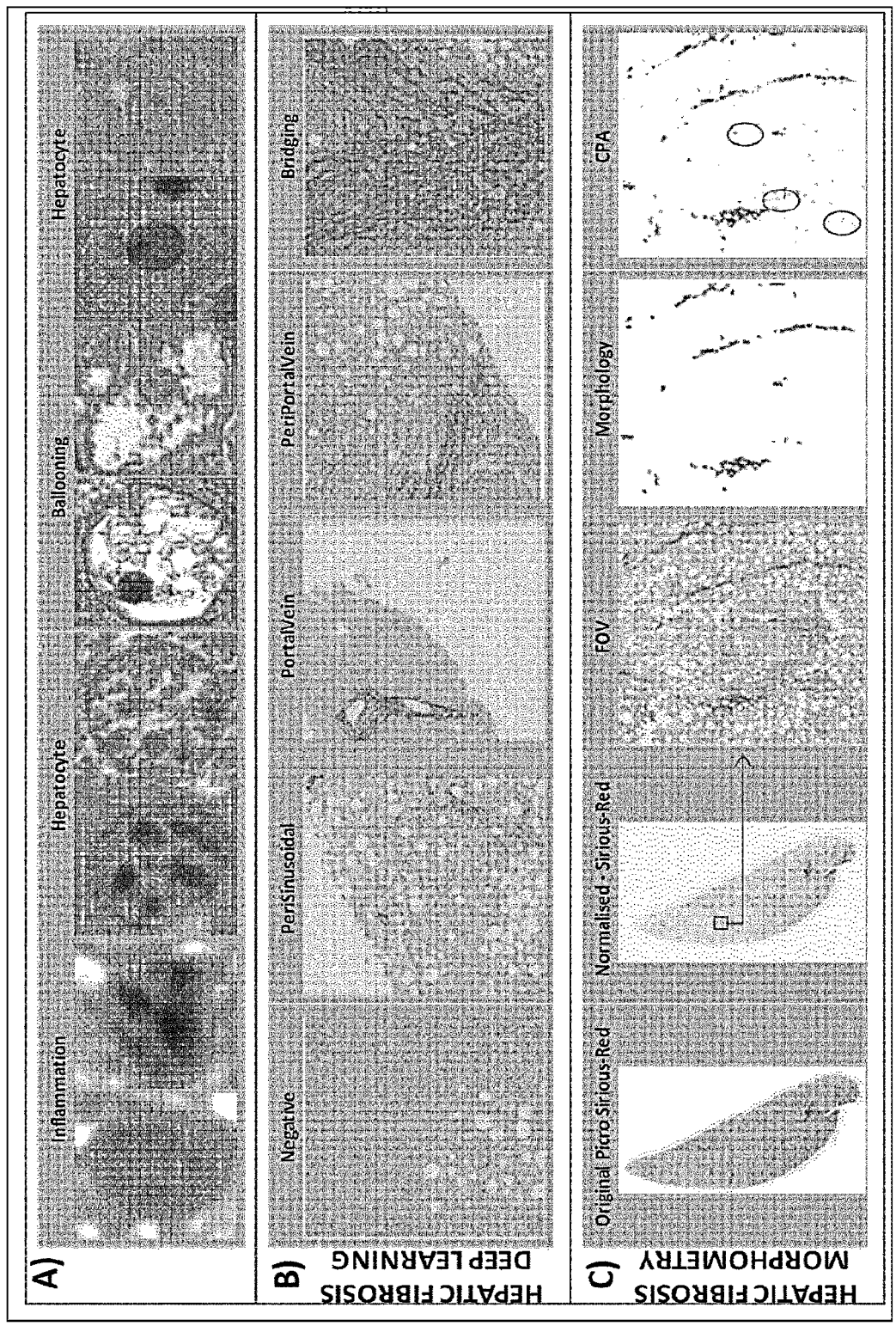

FIG. 4: Illustration of cell-based and fields of view (FOVs) images representing the training and validation set for the development of inflammation, ballooning and fibrosis deep-learning models.

A) Left panel, illustrates cell images representing the training and validation set of inflammatory cell and normal hepatocytes nuclei used for training and validation of the inflammation model. Right panel illustrates few examples of ballooned and normal hepatocytes used for validation of the ballooning model. B) Examples of FOVs representing the five patterns in the training and validation datasets which are automatically recognized by the deep-learning fibrosis model. All FOVs showing only background noise or very little biopsy material (<=5%) are automatically filtered in the earlier pre-processing steps of our computational pathology pipeline. C) Illustration of fibrosis morphometric analysis. From left to right, raw images (first graphic) are normalized and foreground collagen staining (second graphic) is extracted from the background. Normalized collagen images (third graphic) are then analyzed to extract morphological properties of fibrosis septa (fourth graphic) and CPA measurement (fifth graphic, blue circles indicate non-septa collagen areas).

Figure 5:
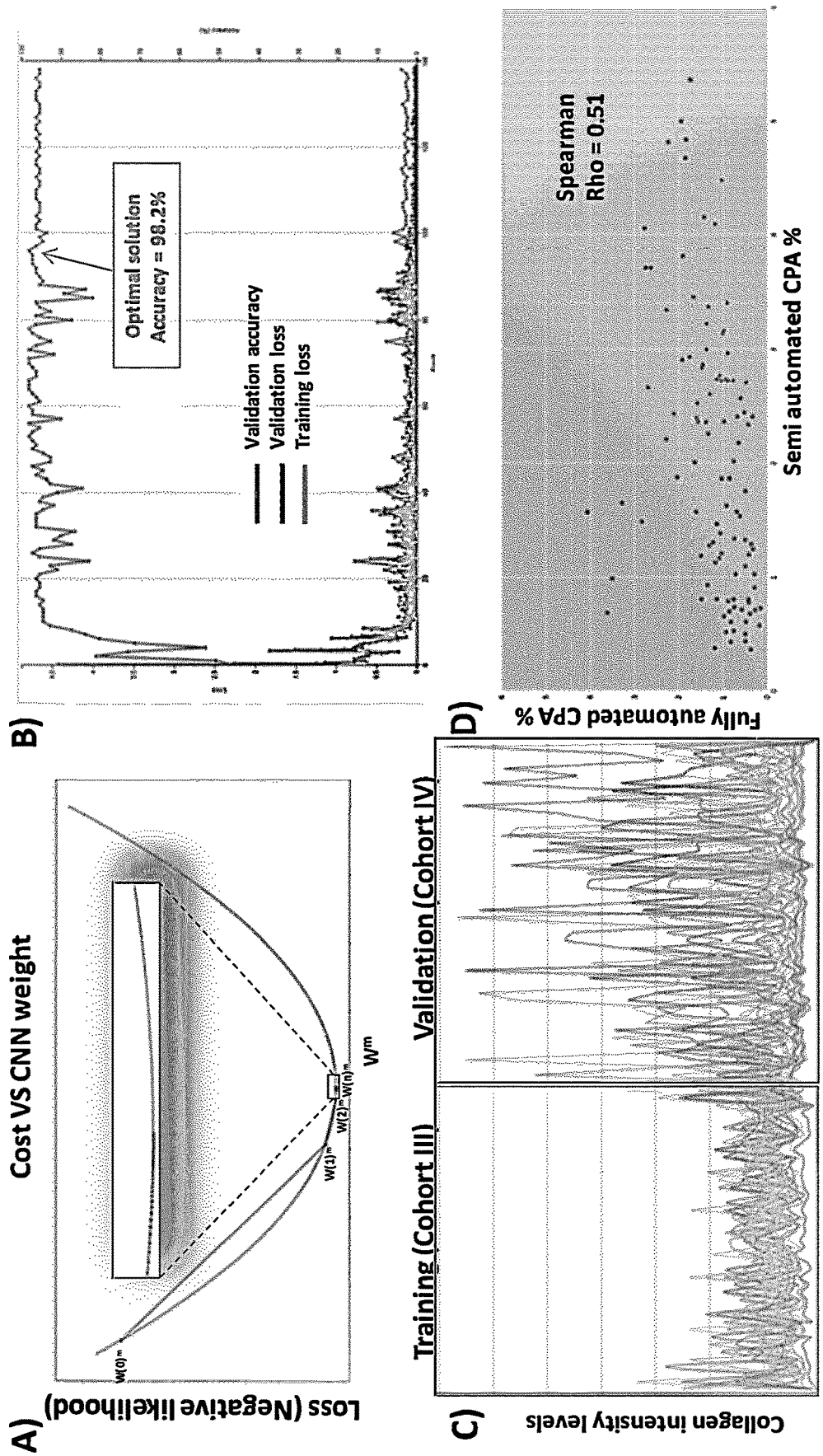

FIG. 5: Results from the development and validation process of the deep-learning models of inflammation, ballooning and fibrosis.

A) Left panel illustrates schematically the approach used to dynamically adapt the learning rate accordingly to learning cycle iteration. Solid red line represents the cost/loss function (i.e. negative likelihood) as a function of the learning cycle iteration, whereas the solid blue line illustrates adaptation of the learning rate (i.e. dynamic decrease) as we approach the local minima. Highlighted solid red line illustrates a second learning process that was implemented to refine the local minima parameters, a process that was repeated several times to get as close as possible to the optimal solution. B) Ballooning model performances on the training and validation sets as a function of the learning iteration cycle. C) Training and validation intensity levels (one line per intensity level across all samples in the study represented in the x-axis) on the training and the validation set. D) Correlation of the semi-automated and fully-automated measurements of CPA in the training cohort.

Figure 6:
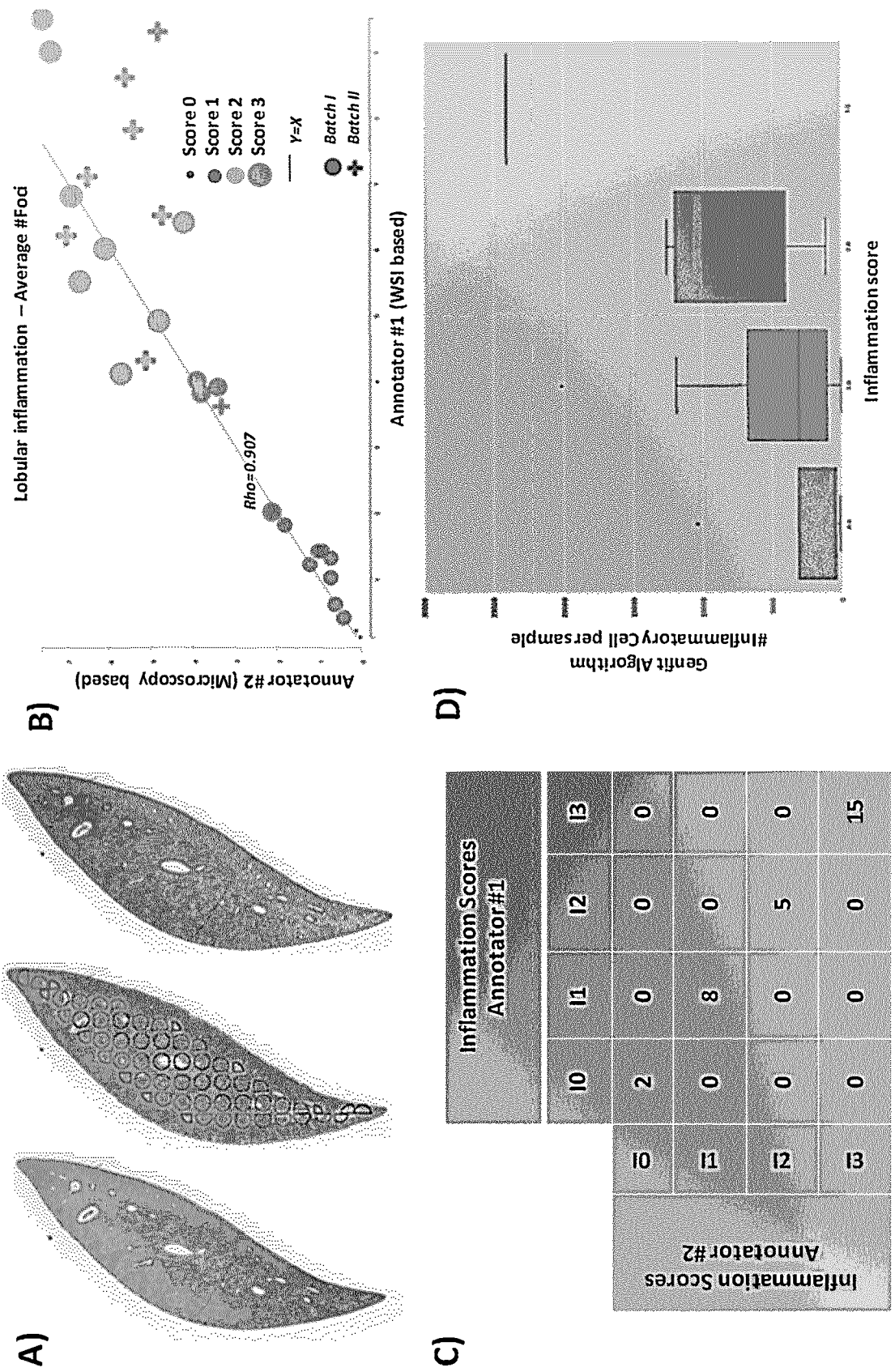

FIG. 6: Results from the validation of the automated inflammation scoring pipeline. A) Illustration of the automated random selection of 10 High Power Fields (HPFs). (From left to right) first image shows an example of raw liver biopsy image (stained with haematoxylin and eosin, H&E), second image shows generation of all possible HPF equivalent to a HPF at 20× under the microscope (in blue are highlighted HPFs with a majority of background and vascular regions, in red are highlighted HPFs valid for inflammation assessment) and third image shows 20 randomly selected HPFs (among all valid HPFs) selected for inflammation scoring (i.e. automated and manual). B) Correlation of manual counting of mean number of foci on 10 randomly selected HPF using a WSI approach and on a standard microscope. C) Table illustrating agreement between microscopy and WSI based inflammation scores (transformed from mean #foci as defined by guidelines (Kliener, 2005, 6:1313-1321)). D) Graphic illustrating the distribution of total number of inflammatory cells (as were automatically recognized by the DL model) per patient (Cohort I) for each inflammation score category (x-axis groups).

Figure 7:
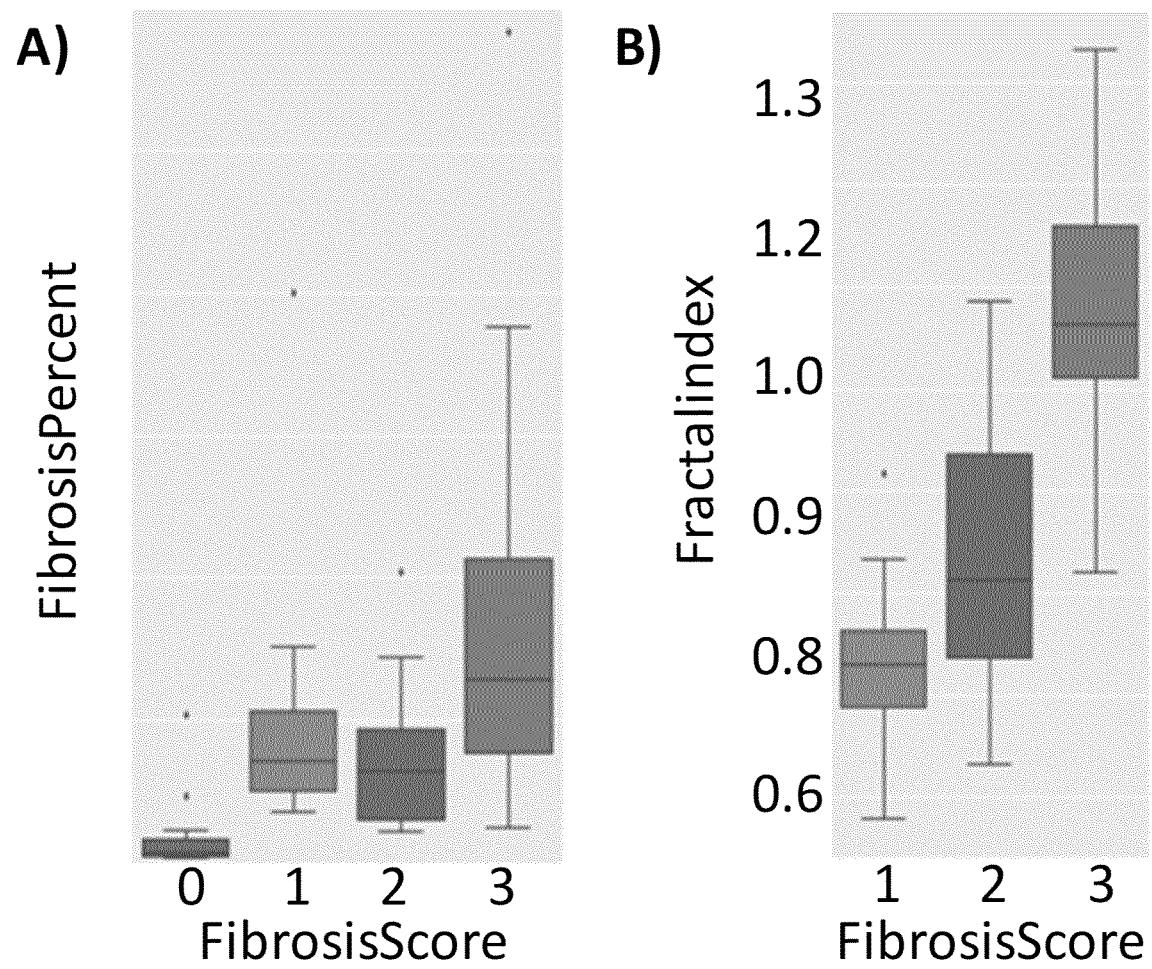

FIG. 7: Results from the development and validation process of the hepatic fibrosis CPA measurement.

A) Distribution of fully automated CPA measurements for each fibrosis score patient group (Cohort VI). B) Distribution of full-automated septa morphology for patients with moderated (F1&F2) and advanced (F3) fibrosis scores (Cohort VI).

Figure 8:
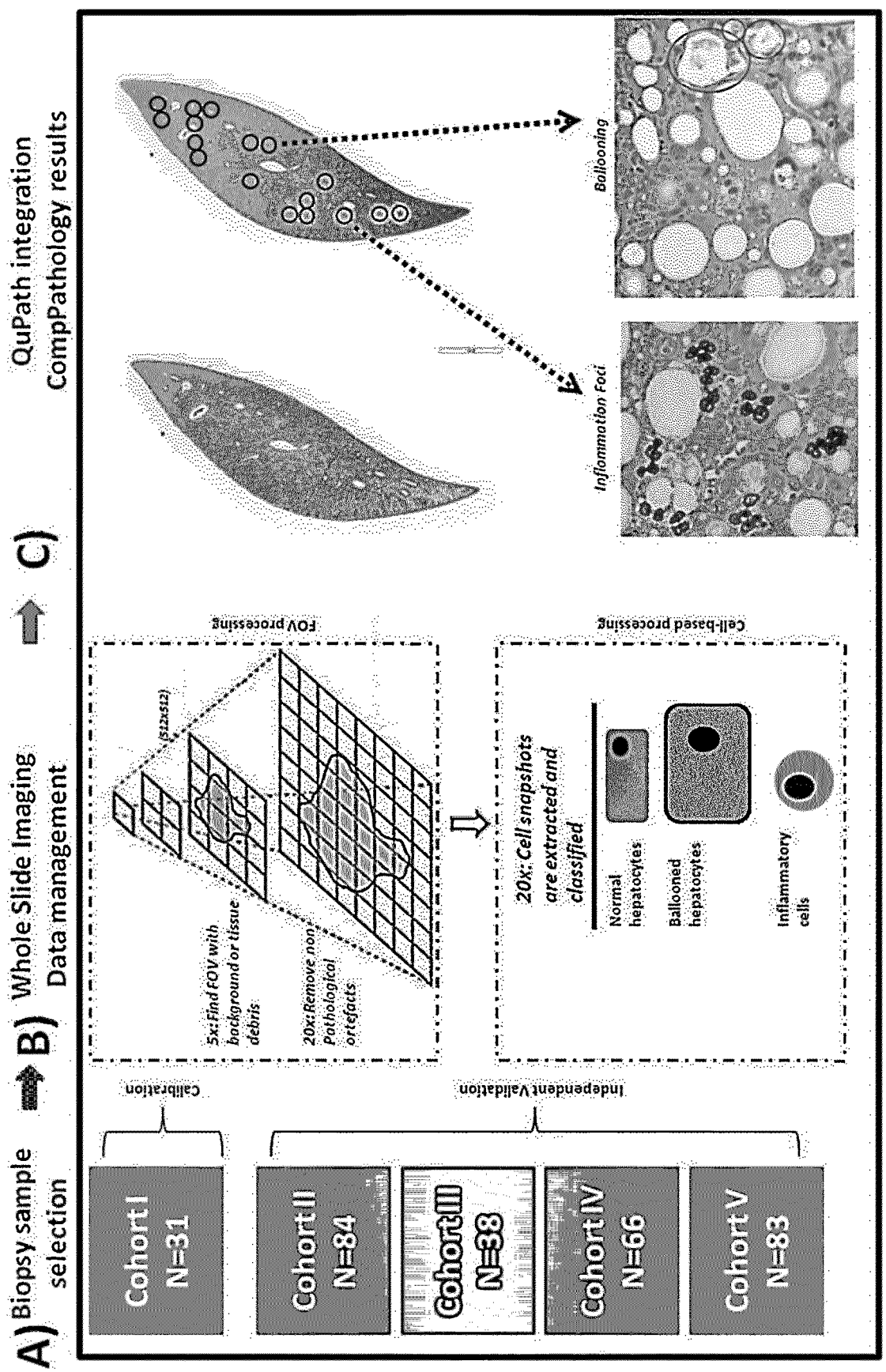

FIG. 8: Schematic representation of data workflow for the automated activity scoring pipeline.

A) Illustration of the different study cohorts used to validate automated scoring pipelines. B) Schematic representation of image manipulation workflow within QuPath open source framework prior to the quantitation process. C) Illustration of the visual mapping of inflammation and activity scoring for the user to validate or to be used as diagnostic aid. Circles on the low resolution tissue section image correspond to the size and shape of a field of view at 20× magnification under an optical microscope. On the bottom part of this section it is illustrated examples of how inflammation foci and ballooned hepatocytes events are annotated in QuPath the to end-user to validate or correct.

Figure 9:
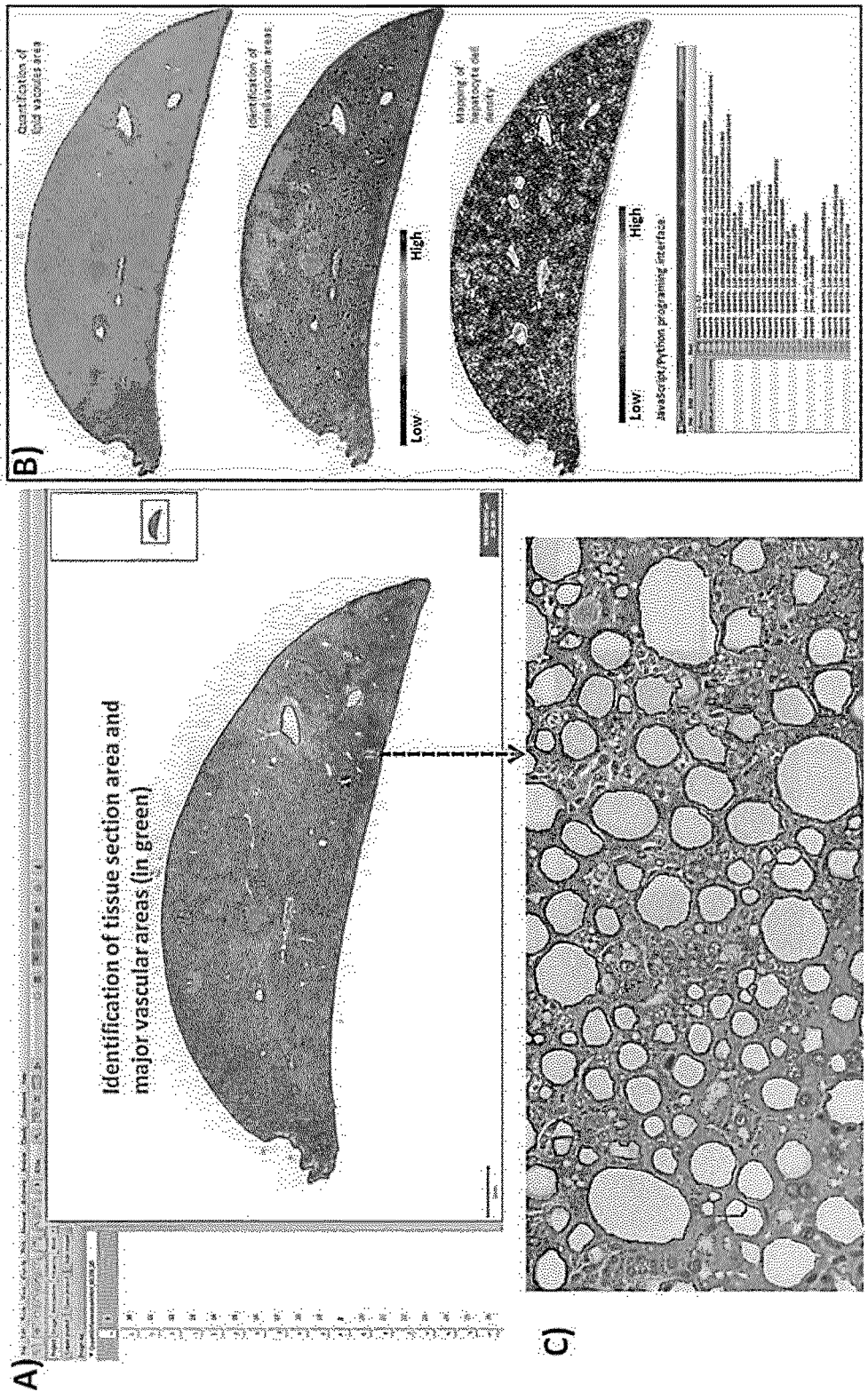

FIG. 9: Integration of steatosis, inflammation and ballooning results to the open-source platform QuPath.

A) View of the QuPath user interface, allowing browsing, project WSI management, image analysis, pattern recognition and data analysis. B) Different image analysis outputs on a liver section stained with H&E, illustrating the data extraction and analysis potential of QuPath. C) Illustration of cell-based results mapping on the digital slide (e.g. lipid vacuoles).

Figure 10:
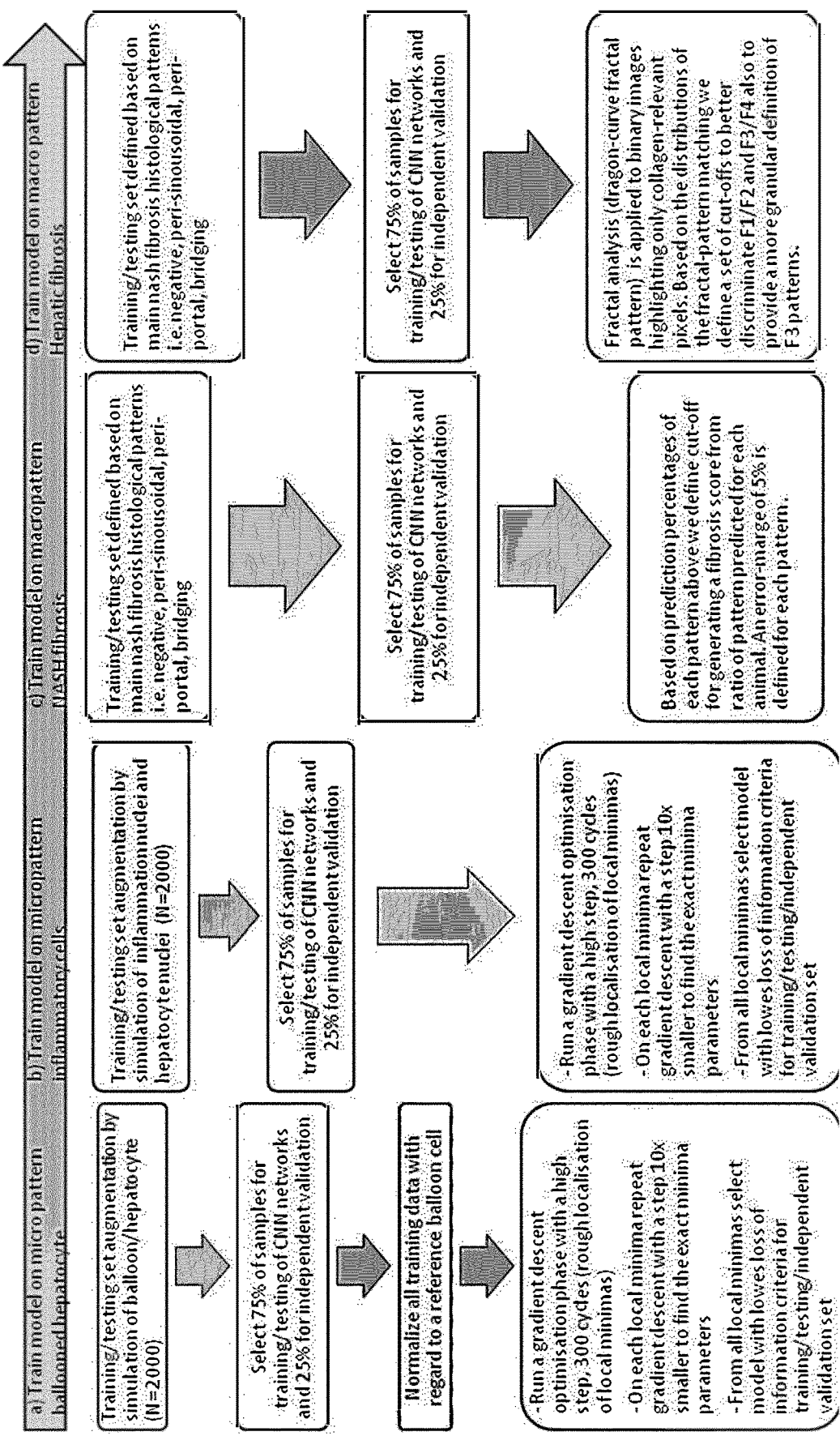

FIG. 10: Phase IV details and workflow for NASH and hepatic fibrosis automated scoring

DETAILED DESCRIPTION OF THE INVENTION

The inventors provide a new method for the automated pattern recognition and scoring method of histological images.

The invention provides a deep-learning framework on a digitalized slide to automatically recognize and score hepatocyte ballooning, hepatic lobular inflammation, NASH fibrosis, and hepatic fibrosis histological patterns at FOV level.

This framework may be further extended to steatosis recognition, quantification, scoring and/or localization on a digitalized slide.

According to the present invention, the term "liver biopsy" is a procedure that involves taking a small piece of liver tissue for examination with a microscope for signs of damage or disease.

According to the present invention, the term "Histological image" is an histopathological slide stained with a staining suitable for the observation of particular cell or tissue features. Hematoxylin and Eosin (H&E) are illustrative stains. Hematoxylin stains nucleic acids and appears blue/purple, while eosin stains proteins and appears pink/red when visualized under a brightfield microscope. So for most tissues, cell nuclei are blue, while cytoplasm can vary from clear to red to purple depending on its constituents.

According to the present invention, the term "steatosis" is usually defined, at the light microscopic level, based on hemotoxylin and eosin (H&E) staining, as clear vacuoles containing lipids. Hepatocellular steatosis is the hallmark of NAFLD, and steatosis in more than 5% of hepatocytes is currently required for the diagnosis of NAFLD.

According to the present invention, the term "macrosteatosis" or "macrovesicular steatosis" correspond to the most common form of fatty degeneration and may be caused by oversupply of lipids.

According to the present invention, the term "microsteatosis" or "microvesicular steatosis is characterized by small intracytoplasmic fat vacuoles (liposomes) which accumulate in the cell. Common causes are tetracyclines, acute fatty liver of pregnancy, Reye's syndrome, and hepatitis C According to the present invention, a "reference image" of a cell or tissue structure is a snapshot which is representative of said cell or tissue structure, as determined by a pathologist. Such a reference image may be submitted to different image treatment to obtain images representing different cell patterns likely to be present in a slide of a liver biopsy. For example, a reference image may be submitted to scaling, staining and/or morphological transformations. Furthermore, a set of reference images may be generated from one or more reference images. For example one reference image may be transformed as mentioned beforehand to obtain at least 2, 3, 4, 5, 6, 7, 8, 9 or at least 10 different transformed images, representing a set of reference images. As an illustration, a set of 1000 reference images may be generated from 100 individual cell or tissue reference images with scaling, staining and morphological modifications, representing each possible cell or tissue pattern.

Scaling staining, and morphological linear modifications may range from 0 up to 20% of the reference image.

In a particular embodiment the scaling, staining, and morphological linear modifications may range from 0 up to 20% of the reference image In a particular embodiment, morphological and scaling modifications may be applied on the form: i.e. linear and affine transformations from 0 up to 20%.

In a more particular embodiment, morphological and scaling modifications may be applied on the form: i.e. linear and affine transformations from 0 up to 10%.

In a particular embodiment, staining modifications may be random transformation of the chromacity from 0 up to 5%.

According to the present invention, a "reference image specific to the stain and pattern annotation" is an image used for staining normalization per pathologic feature of a tissue.

According to the present invention, a "reference image specific to the stain and NASH parameter" is an image used for staining normalization per NASH parameter.

According to the present invention, a "pattern annotation" is defined as the pathologic feature of the tissue. In NAFLD patients, specific pathologic features of the liver tissue may be Hepatocyte Ballooning, Lobular Inflammation, Steatosis, hepatic or NASH Fibrosis According to the present invention, a "micro-pattern" is defined as cell structures, i.e. Ballooned cell, inflammatory cell.

According to the present invention, a "macro-pattern" is defined as adjacent tissue area, i.e. fibrosis.

According to the present invention, the term "hepatocellular ballooning" is usually defined, at the light microscopic level, based on hematoxylin and eosin (H&E) staining, as cellular enlargement 1.5-2 times the normal hepatocyte diameter, with rarefied cytoplasm. It refers more generally to the process of hepatocyte cell death. Of course, in the present invention other staining than H&E may be used to determine the presence of said feature.

According to the present invention, the term "lobular inflammation" refers to the presence of lobular inflammatory foci (grouped inflammatory cells) at microscopic examination of a hematoxylin and eosin (H&E) stained slice of a liver biopsy. Of course, in the present invention other staining than H&E may be used to determine the presence of said feature.

According to the present invention, the term "fibrosis" or "liver fibrosis" refers to the presence of fibrous connective tissue at microscopic examination of a stained (e.g. Hematoxylin and Eosin and Safran (HES), trichrome, Sirius red or picrosirius red staining) slice of a liver biopsy.

According to the present invention, the "Activity index" refers to the sum of hepatocellular ballooning and lobular inflammation scores.

According to the present invention, the "NAFLD-Activity score" or "NAS" refers to the sum of steatosis, hepatocellular ballooning, lobular inflammation scores, as follows:

Steatosis score: 0: <5%; 1: 5-33%; 2: 34-66% and 3: >66%;

Lobular Inflammation score (foci/x20 field): 0: none; 1: <2; 2: 2-4 and 3>4;

Ballooning degeneration score: 0: none; 1: few; 2: many.

According to the present invention, the terms "NAFLD" or "Non Alcoholic Fatty Liver Disease" refers to a condition in which fat is deposited in the liver (hepatic steatosis), with or without signs of inflammation and fibrosis, in the absence of excessive alcohol consumption.

According to the invention, the terms "NAFLD activity level" refer to NAFLD progression and is defined by an increase in the steatosis score, as defined herein. NAFLD activity level also refers to of NAFLD progression towards NASH or Fibrosis and NASH severity According to the invention, the term "NASH" or "Non-Alcoholic SteatoHepatitis" refers to a NAFLD condition characterized by the concomitant presence of liver steatosis, hepatocyte ballooning and liver inflammation at histological examination, (i.e. NAS≥3, with at least 1 point in steatosis, at least 1 point in lobular inflammation and at least 1 point in the hepatocyte ballooning scores) in the absence of excessive alcohol consumption and after excluding other liver diseases like viral hepatitis (HCV, HBV) . . .

According to the invention, the terms "NASH activity level" refer to NASH progression and is defined by an increase in the NAS score above the minimal parameters for defining a NASH, which are S=1, LI=1 and HB=1. NASH activity level also refers to NASH progression towards irreversible NASH and/or fibrosis and NASH severity.

According to the invention, the term "Active-NASH" refers to a NASH characterized by a NAS≥4, with at least 1 point in steatosis, at least 1 point in the lobular inflammation and at least 1 point in the hepatocyte ballooning scores.

According to the present invention, "To-Be-Treated subject" or "TBT subject" is a subject whose disease activity score (e.g. NAS or Activity Index) and/or liver fibrosis stage make the subject eligible to a treatment for NAFLD, NASH and/or liver fibrosis. By opposition a "Not-To-be-treated subject" or "NTBT subject" is a subject whose disease activity score (e.g. NAS or Activity Index) and/or liver fibrosis stage is not high enough to deserve treatment for NAFLD, NASH and/or liver fibrosis. Therefore, a TBT subject is also referred to as "receiver" or "potential receiver" for a NAFLD, NASH and/or liver fibrosis treatment. In the present invention, preferential TBT subjects are:

i) subjects with NASH, ii) subjects with Active-NASH, iii) subjects with liver significant, moderate or severe fibrosis, iv) subjects with NASH and fibrosis.

The definition encompasses various NASH activity values and fibrosis stages defining different variants of the invention.

Preferential variants of the invention are detailed as follows.

First TBT variant (TBT2):

A TBT2 subject is defined as a subject presenting the following liver biopsy-derived grades:

steatosis score≥1 hepatocyte ballooning score≥1 lobular inflammation score≥1

NAS (NAFLD Activity Score)≥4 fibrosis stage≥2 (such as a fibrosis stage equal to 2, 3 or 4, in particular 2 or 3). By extension a NTBT2 subject differs from a TBT2 subject in at least one point lesser grade in steatosis, hepatocyte ballooning, lobular inflammation scores, NAS and/or fibrosis stage.

Second TBT variant (TBT1):

A TBT1 subject is defined as a subject presenting the following liver biopsy-derived grades:

steatosis score≥1 hepatocyte ballooning score≥1 lobular inflammation score≥1

NAS (NAFLD Activity Score)≥4 fibrosis stage≥1 (such as a fibrosis stage equal to 1, 2, 3 or 4).

By extension a NTBT1 subject differs from a TBT1 subject in at least one point lesser grade in steatosis, hepatocyte ballooning, lobular inflammation scores, NAS and/or fibrosis stage Third TBT variant (TBT7):

A TBT7 subject is defined as a subject presenting the following liver biopsy-derived grades:

steatosis score≥1 hepatocyte ballooning score≥1 lobular inflammation score≥1

NAS (NAFLD Activity Score)<4 fibrosis stage=1b, 1c, 2, 3 or 4.

By extension a NTBT7 subject differs from a TBT7 subject in at least one point lesser grade in steatosis, hepatocyte ballooning, lobular inflammation scores, NAS and/or fibrosis stage.

According to the invention, the term "CPA" or "Collagen Proportionate Area" is the total proportion of the collagen stained area to the total tissue area. The label may be picrosirius red or other dyes (i.e. trichrome). CPA is reported at the biopsy level as ratio of total pathological collagen area to the total biopsy tissue area. CPA is an independent predictor of long term outcome in patients with non-alcoholic fatty liver disease.

According to the invention, the term "DL" or "Deep-learning" is a new area of Machine Learning research, which has been introduced with the objective of moving Machine Learning closer to one of its original goals: Artificial Intelligence. Deep Learning is about learning multiple levels of representation and abstraction that help to make sense of data such as images, for pattern analysis and classification.

According to the invention, the term "CNN" or Convolutional neural network is a class of deep, feed-forward artificial neural networks in machine learning that has been applied to analyzing visual imagery (image recognition and classification).

According to the invention, the term "DL model" may use CNN for pattern recognition or analysis, and classification.

The present invention relates to a method for characterizing the occurrence and grade of hepatocyte ballooning in a subject, comprising determining the hepatocyte ballooning score using hepatocyte ballooning DL model in liver biopsies of said subject.

The present invention also relates to a method for characterizing the occurrence and grade of hepatocyte lobular inflammation in a subject, comprising determining the lobular inflammation score using lobular inflammation DL model in liver biopsies of said subject.

The present invention relates to a method for characterizing the occurrence and grade of steatosis in a subject, comprising determining the steatosis score using an automated process in liver biopsies of said subject.

The present invention relates also to dedicated normalization methods for steatosis, hepatocyte ballooning, lobular inflammation, NASH fibrosis and Liver fibrosis.

The present invention relates to the characterization of micro-steatosis and macro-steatosis in a subject is based on pattern recognition, cell size and morphology analysis, and scoring in liver biopsy.

The present invention also relates the localization and disposition of specific histological patterns relative to portal vein, sinusoids, lobular vein, or other substructures, may provide precious complementary informations on liver pathology.

The present invention relates to the full automation of the histological profile analysis.

The present invention relates also to the automation of the quantification of histological NASH parameters.

The present invention further relates to the automation and integration in a bioimage analysis software (in particular: QuPath platform) of the quantification of histological NASH parameters.

The present invention also relates to a method for the determination and scoring of NASH activity index in a subject, comprising determining the hepatocyte ballooning and lobular inflammation scores, in a liver biopsy of said subject.

The present invention also relates to a method for the diagnosis of NASH in a NAFLD patient, comprising determining the hepatocyte ballooning and lobular inflammation scores, using DL models in a liver biopsy of said subject. AI=0 or 1, no NASH; AI>1 with at least HB=1 and LI=1.

The present invention also relates to a method for the determination of occurrence and liver fibrosis stage in a subject, comprising determining the fibrosis score, NASH fibrosis score for DL analysis and hepatic fibrosis score for CPA and morphometric analysis in a liver biopsy of said subject.

As liver fibrosis is a common consequence of most chronic liver diseases, the present invention also relates to diagnosis and detection of significant or advanced liver fibrosis due to other fibrotic liver diseases such as: viral hepatitis (HBV, HCV, . . . ), Alcoholic steatohepatitis, Biliary diseases (Primary biliary cholangitis, Primary Sclerosing cholangitis, Autoimmune hepatitis, Wilson's disease, Alpha1 antitrypsine deficiency).

The present invention also relates to a method for classifying a subject as a potential receiver (TBT) or non-receiver (NTBT) of a treatment for NASH and/or fibrosis, comprising application of hepatocyte ballooning, lobular inflammation and fibrosis DL models, fibrosis morphometric model and steatosis quantification, in a liver biopsy of said subject.

The invention also relates to a method for the prognostic of the risk of NAFLD or NASH activity evolution in the absence of a treatment in a subject, comprising application of hepatocyte ballooning, lobular inflammation and fibrosis DL models, fibrosis morphometric model and steatosis quantification, in a liver biopsy of said subject.

The invention also relates to a method for the prognostic of the risk of fibrosis evolution to cirrhosis and liver clinical outcomes in the absence of treatment in a subject, comprising application of hepatocyte ballooning, lobular inflammation and fibrosis DL models, fibrosis morphometric model, and steatosis quantification, in a liver biopsy of said subject.

The invention also relates to a method for monitoring the evolution (i.e. progression or regression) of NAFLD or NASH activity in a subject, comprising application of hepatocyte ballooning, lobular inflammation and fibrosis DL models, fibrosis morphometric model, and steatosis quantification, in a liver biopsy of said subject.

The invention also relates to a method for monitoring the evolution (i.e. progression or regression) of liver fibrosis in a subject, comprising application of hepatocyte ballooning, lobular inflammation and fibrosis DL models, fibrosis morphometric model, and steatosis quantification, in a liver biopsy of said subject.

The invention also relates to a method for predicting the response of a patient to a specific treatment of NAFLD, NASH and/or liver fibrosis in a subject, comprising application of hepatocyte ballooning, lobular inflammation and fibrosis DL models, fibrosis morphometric model, and steatosis quantification, in a liver biopsy of said subject.

Thus, the invention relates to a method for the diagnosis and detection of NAFLD in a subject, based on application of hepatocyte ballooning, lobular inflammation and fibrosis DL models, fibrosis morphometric model, and steatosis quantification, in a liver biopsy of said subject.

According the present invention, methods are provided to:
characterize the occurrence of hepatic steatosis
characterize the occurrence of hepatocellular or hepatocyte ballooning in a subject
characterize the occurrence of lobular inflammation in a subject
characterize the occurrence of liver fibrosis and NASH fibrosis in a subject
characterize the occurrence of NASH in a subject Thus, according the present invention, methods are provided to:
characterize the occurrence of hepatocellular or hepatocyte ballooning in a subject characterize the occurrence of lobular inflammation in a subject characterize the occurrence of liver fibrosis and NASH fibrosis in a subject characterize the occurrence of NASH in a subject In addition, according to the present invention, methods are provided to:

diagnose the subject to have steatosis and/or a more advanced hepatic steatosis, diagnose the subject to have hepatocellular ballooning and/or a more advanced hepatocellular ballooning score, diagnose the subject to have lobular inflammation and/or more advanced lobular inflammation score, diagnose the subject to have liver fibrosis and/or a more advanced liver fibrosis stage and NASH fibrosis, diagnose the subject to have NASH among NAFLD patients, Furthermore, according to the present invention, methods are provided to:

diagnose the subject to have hepatocellular ballooning and/or a more advanced hepatocellular ballooning score, diagnose the subject to have lobular inflammation and/or more advanced lobular inflammation score, diagnose the subject to have liver fibrosis and/or a more advanced liver fibrosis stage and NASH fibrosis, diagnose the subject to have NASH among NAFLD patients, Furthermore, the methods according to the present invention allow to:

determine the steatosis score, determine the hepatocyte ballooning score, determine the lobular inflammation score, determine the NASH related activity index, determine the NASH fibrosis stage in a subject determine the hepatic fibrosis stage in a subject, determine the severity of a NASH in a subject, determine the progression or regression of the pathology in a NASH patient.

Furthermore, the methods according to the present invention allow to:

determine the hepatocyte ballooning score, determine the lobular inflammation score, determine the NASH related activity index, determine the NASH fibrosis stage in a subject determine the hepatic fibrosis stage in a subject, determine the severity of a NASH in a subject, determine the progression or regression of the pathology in a NASH patient.

In addition, according to the present invention, methods are provided to:

determine microsteatosis or macrosteatosis determine lobular or portal inflammation determine perisinusoidal, periportal, portal fibrosis determine specific location of NASH parameters (location of foci, location of balloon cells . . . ) in the tissue biopsy determine qualitative mapping of interesting biological information Moreover, the methods according to the present invention allow to:

classify a subject as a receiver or non-receiver of a treatment for NAFLD, classify a subject as a receiver or non-receiver of a treatment for NASH, classify a subject as a receiver or non-receiver of a treatment for liver fibrosis, classify a subject as a receiver or non-receiver of a treatment for hepatocellular ballooning, classify a subject as a receiver or non-receiver of a treatment for lobular inflammation, Furthermore, the methods according to the present invention allow to:

classify a subject as a receiver or non-receiver of a treatment for NASH, classify a subject as a receiver or non-receiver of a treatment for liver fibrosis, classify a subject as a receiver or non-receiver of a treatment for hepatocellular ballooning, classify a subject as a receiver or non-receiver of a treatment for lobular inflammation, Furthermore, the methods according to the present invention allow to:

assess the efficacy of a medical treatment based on a drug administration to treat NAFLD disease, assess the efficacy of a medical treatment based on a drug administration to treat NASH disease, assess the efficacy of a medical treatment based on a drug administration to treat fibrosis disease, assess the efficacy of a medical treatment based on a drug administration to treat hepatocellular ballooning disease, assess the efficacy of a medical treatment based on a drug administration to treat lobular inflammation disease.

Furthermore, the methods according to the present invention allow to:

assess the efficacy of a medical treatment based on a drug administration to treat NASH disease, assess the efficacy of a medical treatment based on a drug administration to treat fibrosis disease, assess the efficacy of a medical treatment based on a drug administration to treat hepatocellular ballooning disease, assess the efficacy of a medical treatment based on a drug administration to treat lobular inflammation disease.

Furthermore, the methods according to the present invention allow to:

determine the progression or regression of the pathology in a NAFLD patient after the administration of a medical treatment, determine the progression or regression of the pathology in a NASH patient after the administration of a medical treatment, determine the progression or regression of the pathology in a patient suffering from fibrosis after the administration of a medical treatment, determine the progression or regression of the pathology in a patient suffering from hepatocellular ballooning disease after the administration of a medical treatment, determine the progression or regression of the pathology in a patient suffering from lobular inflammation disease after the administration of a medical treatment.

Furthermore, the methods according to the present invention allow to:

determine the progression or regression of the pathology in a NASH patient after the administration of a medical treatment, determine the progression or regression of the pathology in a patient suffering from fibrosis after the administration of a medical treatment, determine the progression or regression of the pathology in a patient suffering from hepatocellular ballooning disease after the administration of a medical treatment, determine the progression or regression of the pathology in a patient suffering from lobular inflammation disease after the administration of a medical treatment.

Furthermore, the methods according to the present invention allow to:

predict if a patient will be receptive or not, i.e. (potentially) responder or (potentially) non-responder to a medical treatment to treat NAFLD disease, predict if a patient will be receptive or not, i.e. (potentially) responder or (potentially) non-responder to a medical treatment to treat NASH disease, predict if a patient will be receptive or not, i.e. (potentially) responder or (potentially) non-responder to a medical treatment to treat liver fibrosis, predict if a patient will be receptive or not, i.e. (potentially) responder or (potentially) non-responder to a medical treatment to treat a hepatocellular disease, predict if a patient will be receptive or not, i.e. (potentially) responder or (potentially) non-responder to a medical treatment to treat a lobular inflammation disease.

Furthermore, the methods according to the present invention allow to:

predict if a patient will be receptive or not, i.e. (potentially) responder or (potentially) non-responder to a medical treatment to treat NASH disease, predict if a patient will be receptive or not, i.e. (potentially) responder or (potentially) non-responder to a medical treatment to treat liver fibrosis, predict if a patient will be receptive or not, i.e. (potentially) responder or (potentially) non-responder to a medical treatment to treat a hepatocellular disease, predict if a patient will be receptive or not, i.e. (potentially) responder or (potentially) non-responder to a medical treatment to treat a lobular inflammation disease.

In some embodiments, the methods for determining whether a subject has NAFLD comprises providing a liver biopsy from a subject, in particular a subject suspected of having the assessed condition, and applying DL models on steatosis parameter indicates the presence of the assessed condition.

In some embodiments, the methods for determining whether a subject has NASH, or Active-NASH or significant liver fibrosis, or lobular inflammation, or hepatocyte ballooning or for determining if a subject is a drug receiver (TBT) or a potential responder to a specific drug comprise providing a liver biopsy from a subject suspected of having the assessed condition, and applying DL models on individual histological parameters indicates the presence or the absence of the assessed condition, or the diagnosis of the subject as having NASH, or significant liver fibrosis, or lobular inflammation, or hepatocyte ballooning or the subject as being a potential drug receiver (TBT) or responder.

In particular embodiments, the subject is suffering from NAFLD, the method of the invention thereby allowing determining the efficacy of a drug for the treatment of the NAFLD disease, classifying the subject as responder/non-responder to a treatment for NAFLD, or monitoring the evolution of the NAFLD state of the subject.

In particular embodiments, the subject is suffering from NASH, the method of the invention thereby allowing determining the efficacy of a drug for the treatment of the NASH disease, classifying the subject as responder/non-responder to a treatment for NASH, or monitoring the evolution of the NASH state of the subject.

Preprocessing of histological images up to pattern recognition:

The method of the invention analyzes histological images.

Histological image is an histopathological slide stained. One skilled in the art knows how to generate such images. The main steps are tissue collection, processing which involves chemically and physically stabilizing the tissue, embedding in a block of support material, sectioning and staining to create contrast.

In a particular embodiment, the staining implemented allows to differentiate cellular components or constituents. For example, the staining may be suitable to allow to differentiate nuclei, cytosol and tissue components.

Illustrative stains include oil red 0, Hematoxylin and Eosin, Sirius Ped, Trichrome, Hematocylin/Eosin/Safran (HES), PicroSirius red, keratin 18, fluorescent stains, and immunostaining.

In a particular embodiment, the stains implemented in the invention are hematoxylin and eosin (H&E) on a first slide and Picrosirius red on a second slide.

In a particular embodiment, the stains may be Trichrome on one slide.

The histological image is then digitalized.

Image digitalization

The methods of the invention are based on the analysis of digitalized images of liver biopsies. The image acquisition may be performed by any image acquisition means. For example, the image is digitalized with a whole-slide scanner or a camera.

In a particular embodiment, the acquisition generates high-resolution Whole Slide Image (WSI). Such high resolution may range between 1,000 x 1,000 pixels and 1,000× 200,000 pixels, such as between 2,000×2,000 pixels and 2,000×200,000 pixels, for example between 3,000×5,000 pixels and 3,000×150,000 pixels, such as between 10,000× 20,000 pixels and 10,000×150,000 pixels. For example, an image with a resolution of 20,000×140,000 pixels may be generated for a slide 5 mm×35 mm at the resolution of 0.25 pm per pixel.

In another embodiment, digitalization is carried out in a proprietary format (e.g. of the svs (Leica) or mrx (3DHistech) type), the digital image may then be transformed into another format (in particular as DICOM format tile based) more suitable for a computation pathology workflow. Such suitable format include tile-based formats such as the DICOM format.

In another embodiment, digitalization is directly carried out in a format suitable for a computation pathology workflow or bioimage analysis software, such as a tile-based format, for example the DICOM format.

The digitalized slide may then be decomposed in tiles of a lower size. For example, the digitalized slide may be decomposed in tiles whose size correspond to a tissue or cell pattern of interest. In a particular embodiment, the tiles are of a size slightly higher than the expected size of a cell (taking into account the fact that the cells may be ballooned, i.e. possibly having a size 2 times higher than a normal cell, or the fact that biopsy slide preparation may deform the cells). For example tiles may be generated having a size of 512×512 pixels.

Region of interest identification

For analysis, each source of variability may represent a significant obstacle. Tissue that is poorly fixed will not cut well and may have a blurry appearance, removing important cues such as edges. Tissue that has been dried out may be shrunken and have poor morphology and stain contrast. Sectioning artifacts are some of the most commonly encountered and can produce folds in the tissue, chatter artifacts from a dull blade (seen as alternating light and dark regions), or missing pieces of the tissue.

The method of the invention is implemented on a selected tissue zone on the histological image to be analyzed.

According to a particular embodiment, a pattern recognition model is implemented on the slide image to allow to differentiate the tissue from the background total area (expressed in mm2, for example) of the slide. The outline of the biopsy part excluding hollow and non tissue areas of the slide is defined and represents the tissue biopsy total area. The complementary of the tissue biopsy area is defined as the slide background total area.

In a particular embodiment, the pattern recognition is applied to the whole slide image. In a further particular embodiment, the pattern recognition is carried out to the 5X representation of the whole slide image.

In another particular embodiment, the pattern recognition is applied to the 5X representation of the whole slide image stained to differentiate cellular compartments and/or fibrosis, such as Picrosirus Red.

The pattern recognition model is applied to exclude tissue-folding artifacts as well as small isolated areas representing air-bubbles, tissue debris and dust.

The method of the invention provides a selected tissue zone on histological image to analyze.

Staining normalization

Staining may be a critical source of variability because it produces the color and contrast on the slide. Staining artifacts can include light staining with either hematoxylin or eosin, precipitated hematoxylin (seen as blue chunks under the microscope), or lack of staining with either hematoxylin, eosin, or both. These artifacts are well understood by pathologists, but may be problematic for automated histology analysis systems that rely on color. Staining normalization is thus preferably done for automated histology image analysis.

In a particular embodiment, staining normalization uses color normalization techniques such as histogram equalization.

In another particular embodiment, the histological image is separated into hematoxylin-only (H-only) and eosin-only (E-only) images (sometimes called color deconvolution), then these images are normalized separately and then recombined.

In another embodiment a different approach is to estimate the single-stain images directly.

In another embodiment a different approach is the color inversion technique.

In a preferred embodiment, from an image at 20 X, staining is deconvolved from any additional stain, counterstaining and normalized against a reference image specific to the stain and the pattern annotation.

In a preferred embodiment, the standardized image allows an automated analysis.

Cell structures identification

The method of the invention may identify cell structures on standardized histological images.

Nucleus detection Nucleus detection in histology images is challenging because nuclei can be tightly clustered and vary in size, shape, and color depending on their cell type. Basic approaches to nucleus detection involve color clustering of the pixels.

In a particular embodiment, from an image at 20 X staining of cell nuclei is deconvolved from any additional stain, counterstaining.

The nuclei staining morphological operations are applied to enhance circular, roundish structures.

In another embodiment, other approaches using active contours are used to refine nuclei initial color segmentation, detect nucleus seed point, or frame nucleus detection as a classification problem.

In a particular embodiment, nuclei below a certain threshold for area (10 pixels), circularity (correlation with perfect circularity=0.7), or roundness (correlation with perfect circularity=0.7) are filtered.

In a preferred embodiment, the nuclei staining morphological operations are applied to enhance circular, roundish structures, and the resulting image is subjected to an adaptive robust background segmentation algorithm to segment all cell nuclei. Nuclei below a certain threshold for area, circularity and roundness are filtered.

Cytosol extension localization

Approaches to find cytosol extension involve color clustering of the pixels. In a particular embodiment, using the center of the nucleus, the extension of the cytosol is simulated by an iterative mask growing process providing there is no more staining or that the border of a neighboring cell is reached.

In another embodiment, using the center of the nucleus and the additional stains, the extension of the cytosol is simulated by an iterative mask growing process providing there is no more staining or that the border of a neighboring cell is reached.

The extended cell area is extracted from the original image and defines a cell-snapshot image. The cell-snapshot is defined as the bounding box.

Extraction of individual cell images (micro pattern)

The method of the invention extracts individual cell images from cell structures on standardized histological images.

Current methods rely on histology-specific features to extract cell-snapshot.

In a particular embodiment, normalization is performed on individual image with a reference image of the cell structure.

In a preferred embodiment, cell-snapshot is extracted and normalized against a reference image chromacity profile (one profile per stain combinations).

An illustrative normalization process may involve: deconvolution of main staining chromacity channels for cell snapshot, deconvolution of reference profile stining chromacity channels, robust z-scoring of each channel from the cell snapshot with regard to the reference profile, and merging of normalized deconvolved channels into one cell-snapshot image.

Extraction of adjacent tissue area (macro pattern)

The method of the invention may also extract adjacent cell tissue area from cell structures on standardized histological images.

Basic approaches to find adjacent tissue involve color clustering of the pixels.

In a particular embodiment, each cell image or FOV is normalized with a referent image.

In a particular embodiment, normalization is performed on individual image with a reference image chromacity profile.

In a preferred embodiment, micropattern is extracted and normalized against a reference image chromacity profile (one profile per stain combinations).

Normalization process involves: deconvolution of main staining chromacity channels for adjacent cell tissue area, deconvolution of reference profile staining chromacity channels, robust z-scoring of each channel from the adjacent cell tissue area with regard to the reference profile, merging of normalized deconvolved channels into one adjacent cell tissue area image.

Method for scoring Hepatocyte Ballooning

Image acquisition, digitalization, region of interest identification, normalization and localization of micro and macro pattern are performed beforehand.

In a preferred embodiment, the staining is performed with H&E.

In a further particular embodiment, the reading is performed on an image at magnification X20.

The method of the invention may automatically identify ballooned cells, quantify the number of ballooned cells and score the hepatocyte ballooning on a normalized histological whole tissue image. The pattern recognition approach and the Balloon cell detection DL model to differentiate ballooned hepatocytes and normal hepatocytes based on a pattern recognition model and morphological criteria of balloon hepatocytes are applied.

The model on micro pattern ballooned hepatocyte is applied on all cell snapshots to compute class probability and predicted class label (Highest probability label) against a reference image of cell structure.

In a particular embodiment the prediction probability to identify ballooned hepatocytes with the optimal balloon cell detection DL model is higher than 90%.

In a preferred embodiment the prediction probability to identify ballooned hepatocytes with the optimal balloon cell detection DL model is higher than 95%.

In a particular embodiment, the loss of keratin 8/18 immunostaining of the cytoplasm may confirm the identification of ballooned cells.

The total number of ballooned cells may be expressed as a percentage of ballooned cells on total number of cells or as a Hepatocyte Ballooning score according to the NASH Clinical Research Network (CRN): Hepatocyte Ballooning score=0 corresponds to "None" in the NAFLD Activity Score, Hepatocyte Ballooning score=1 corresponds to "Few balloon cells", and Hepatocyte Ballooning score=2 corresponds "Many cells/prominent ballooning".

In a particular embodiment, Hepatocyte Ballooning score=0 may correspond to a mean of 0.02% of ballooned hepatocytes among all hepatocytes, Hepatocyte Ballooning score=1 may correspond to a mean of 0.11% of ballooned hepatocytes, and Hepatocyte Ballooning score=2 may correspond to a mean of 0.51% of ballooned hepatocytes.

The pattern recognition and scoring balloon cell DL model for hepatocyte ballooning may be integrated in an open-source computational pathology software or bioimage analysis software (such as QuPath) to increase user acceptance and experience.

The location of ballooned cell may provide interesting biological information.

In a particular embodiment, the qualitative mapping of interesting biological information may be performed when the pattern recognition and scoring balloon cell DL model (ballooning pipeline) is integrated into a computational pathology software or bioimage analysis software (such as QuPath).

Method for scoring Lobular Inflammation

Image acquisition, digitalization, region of interest identification, normalization and localization of micro and macro pattern are performed beforehand.

In a preferred embodiment, the staining is performed with H&E or H&E and Picrosirius red.

In a further particular embodiment, the reading is performed on an image at magnification X20.

In a particular embodiment, all FOVs equivalent to a 20 X high power field under a microscope are determined.

Fields of view (FOVs) with region of interest are determined randomly on the whole slide image by the computer.

In a particular embodiment, all FOVs on the whole slide image are determined. In particular, said FOVs are equivalent to a 20 X high power field under a microscope In a further particular embodiment, a number of FOVs is automatically and randomly selected by the computer program. For example, 2, 3, 4, 5, 6, 7, 8, 9, 10, 11, 12, 13, 14, 15, 16, 17, 18, 19, 20 or more than 40 FOVs may be randomly selected. In a particular embodiment, the number of FOVs selected ranges from 5 and 15 FOVs. In a particular embodiment, this number ranges from 8 to 12 FOVs, in particular from 9 and 11 FOVs, such as 10 FOVs with region of interest which are selected on the whole slide image.

These randomly selected FOVs represent an automated selection of potential area of further study whose interest may be further validated by an experimented operator, thereby providing a help to the experimented operator, or automatically validated by the model of the present invention.

In a particular embodiment, the selection of FOVs further comprises manually specified FOVs by one or more users.

The portal regions are excluded from the reading of lobular inflammation.

In a particular embodiment, fields of view with region of interest are selected from a set of randomly generated FOVs in non-portal regions.

In a more particular embodiment, fields of view with region of interest are selected from a set of randomly generated FOVs in intra-lobular regions.

In a particular embodiment, fields of view are selected by the model and validated by the model or by an experimented operator.

In a particular embodiment, fields of view are generated in intra-lobular regions by the inflammatory cell DL model and randomly proposed to the experimented annotator to validate the selected fields, in particular 10 fields.

The method of the invention may automatically identify inflammatory foci, quantify the number of inflammatory foci and score the Lobular Inflammation on a normalized histological image. The pattern recognition approach and the inflammatory cell DL model to differentiate inflammatory cells and other cells are applied. The pattern recognition approach and the model to recognize portal regions areas from a digitalized biopsy image are applied.

The model on micro pattern inflammatory cells is applied on all cell snapshots to compute class probability and predicted class label (Highest probability label) against a reference image of cell structure.

In a particular embodiment the prediction probability to identify inflammatory cells or foci with the optimal inflammatory cell detection model is higher than 90%.

In a preferred embodiment the prediction probability to identify inflammatory cells or foci with the optimal inflammatory cell detection model is higher than 95%.

The mean number of inflammatory foci on 10 selected fields of view is converted as a lobular inflammation score.

In a particular embodiment, the score is according to the NASH Clinical Research Network (CRN): Lobular Inflammation score=0 corresponds to "no foci" in the NAFLD Activity Score, Lobular Inflammation score=1 corresponds to "<2 foci/ 200X", Lobular Inflammation score=2 corresponds "2-4 foci/200X", and Lobular Inflammation score=3 corresponds to ">4 foci/200X".

In a particular embodiment the mean number of inflammatory foci on 10 FOVs is not converted as a score and follows a linear evolution.

The pattern recognition and scoring inflammatory cell DL model for liver inflammation may be integrated in an open-source computational pathology software or bioimage analysis software (such as QuPath) to increase user acceptance and experience.

The location of inflammatory cell or foci may provide interesting biological information.

In a particular embodiment, the qualitative mapping of interesting biological information may be performed when the pattern recognition and scoring inflammatory cell DL model (inflammatory pipeline) is integrated into a computational pathology software or bioimage analysis software (in particular QuPath).

Method for scoring Steatosis

Image acquisition, digitalization, region of interest identification are performed.

In a preferred embodiment, the staining is performed with H&E.

In a further particular embodiment, the reading is performed on an image at magnification X5.

Staining normalization is performed for each field of view with the determination of a threshold to differentiate cellular structures and vacuoles The method of the invention may automatically identify lipid vacuoles, quantify the area of lipids and score the steatosis on a normalized histological image. The method of pattern recognition and scoring the steatosis area differentiates lipid vacuoles and white areas, based on a pattern recognition model and morphological criteria of lipid vacuoles. The model on micro-pattern lipid vacuoles is applied on all cell snapshots.

In a particular embodiment, one threshold is determined per field of view to differentiate lipid vacuoles from cellular structures.

The pattern recognition approach and scoring the steatosis area model selectively filters out white areas that are not morphologically similar to lipid vacuoles (too small or big enough but not corresponding to pre-defined morphological properties).

The total area of steatosis is expressed as a Steatosis score according to the NASH Clinical Research Network (CRN): Steatosis score=0 corresponds to "<5%" in the NAFLD Activity Score, Steatosis score=1 corresponds to "5-33%", Steatosis score=2 corresponds to "33-66%", and Steatosis score=3 corresponds to ">66%".

In a particular embodiment, the total area of steatosis is expressed as a percentage of whole tissue regions.

In a particular embodiment microsteatosis may be differentiated from macrosteatosis.

In a particular embodiment, the location of steatosis may provide interesting biological information.

In another particular embodiment steatosic cell counts may replace the total area of steatosis.

The pattern recognition and scoring steatosis area model for steatosis may be integrated in a open-source computational pathology software or bioimage analysis software (such as QuPath) to increase user acceptance and experience.

In a particular embodiment, the qualitative mapping of interesting biological information may be performed when the pattern recognition and scoring steatosis area DL model is integrated into a computational pathology software or bioimage analysis software (such as QuPath).

Method for scoring NASH Fibrosis

Image acquisition, digitalization, region of interest identification, normalization and localization of micro and macro pattern are performed beforehand.

In a preferred embodiment, the staining is performed with H&E or H&E and Picrosirius red. In a further particular embodiment, the reading is performed on an image at magnification X5.

The pattern recognition and scoring NASH fibrosis model on macro pattern NASH fibrosis is applied to all pre-normalized FOVs of the whole slide image.

A NASH fibrosis score based on NASH CRN/Kleiner is defined: Fibrosis Stage=0 "None", Fibrosis Stage=1 "perisinusoidal (mild to moderate) or periportal", Fibrosis Stage=2 "perisinusoidal and periportal", Fibrosis Stage=3 "bridging fibrosis", and Fibrosis Stage=4 "cirrhosis".

In a particular embodiment portal and periportal fibrosis may be differentiated from sinusoidal or perisinusoidal fibrosis.

In a further particular embodiment, bridging fibrosis may be diagnosed.

The pattern recognition and scoring model for NASH fibrosis may be integrated in a open-source computational pathology software or bioimage analysis software (such as QuPath) to increase user acceptance and experience.

The location of NASH fibrosis may provide interesting biological information.

In a particular embodiment, the qualitative mapping of interesting biological information may be performed when the pattern recognition and scoring NASH fibrosis DL model (inflammatory pipeline) is integrated into a computational pathology software or bioimage analysis software (such as QuPath).

Method for scoring Hepatic Fibrosis

Image acquisition, digitalization, region of interest identification, normalization and localization of micro and macro pattern are performed beforehand.

In a preferred embodiment, the staining is performed with H&E or H&E and Picrosirius red.

In a further particular embodiment, the reading is performed on an image at magnification X5.

The pattern recognition and scoring model on macro pattern Hepatic fibrosis is applied to all pre-normalized FOVs of the whole slide image.

A hepatic fibrosis score is defined as a mean fractal index over all FOVs, a mean fractal index over all FOVs excluding FOVs predicted as portal area, or a mean fractal index per category of FOVs.

The pattern recognition and scoring model for hepatic fibrosis may be integrated in a open-source computational pathology software or bioimage analysis software (such as QuPath) to increase user acceptance and experience.

The location of hepatic fibrosis may provide interesting biological information.

In a particular embodiment, the qualitative mapping of interesting biological information may be performed when the pattern recognition and scoring hepatic fibrosis DL model (inflammatory pipeline) is integrated into a computational pathology software or bioimage analysis softwarer (such as QuPath).

According to a particular embodiment, sequential operations for this novel pattern recognition and scoring automated method of liver histological slides are provided and describe the innovative functionalities of the computational pathology pipeline. Illustratively, phases 1 to 4 below are provided as an example of a complete analysis carried out according to the invention.

Phase-1

Digitalization: A glass slide is digitalized. The inventors have digitalized the slides under a proprietary format of type sys (Leica) or mrxs (3DHistech), but the acquisition may be performed by any other image reader. According to another embodiment, digitalization is carried out in a format suitable for a computation pathology workflow, such as the DICOM format, which is tile-based.

Storage: Digital files are then linked to the biomedical relevant information in a database.

Reformating: if digitalization was carried out under a proprietary format, the digital image under the proprietary format is then transformed into another format (such as DICOM format, tile-based) more suitable for a computation pathology workflow, for example using a free software (such as OpenSlide).

Phase-2

Find Tissue: A pattern recognition model is applied to the 5× representation of a WSI (slides stained with a standard H&E/Picro-sirious). The outline of the biopsy part excluding hollow and non-tissue areas of the slide is defined.

Find Slide Background: A pattern recognition model is applied to the 5× representation of a WSI (slides stained with a standard H&E/Picro-sirious). The outline of the slide background part excluding hollow and non-tissue areas of the slide is defined is defined. From the total WSI area, the complementary of slide background total area (in mm2) is defined as the tissue biopsy total area.

Find Tissue and Slide Artifacts: A pattern recognition model is applied to the 5× representation of a WSI (slides stained with a standard hematoxylin-eosin (H&E) staining/Picro-sirious). Tissue-folding and staining artifacts as well as small isolated areas representing air-bubbles, tissue debris and dust are automatically identified and outlined.

Phase-3

Find Cell Nuclei:

From the original image at 20×, staining of cell nuclei is first deconvolved from any additional stain, counterstaining.

On the nuclei staining morphological operations are applied to enhance circular, roundish structures.

On the resulting image from the previous step an adaptive robust background segmentation algorithm is applied to segment all cell nuclei.

Nuclei below a certain threshold for area, circularity and roundness are filtered.

A bounding box is defined around each nuclei.

Find Cell Cytosol Extention:

Using the center of the nucleus and the additional stains the extension of the cytosol is simulated by an iterative mask growing process providing there is no more staining or that the border of a neighboring cell is reached.

Maximum bounding box is defined based the extended cell area and is extracted from the original image defining the cell-snapshot image.

Cell-snapshot image is defined as the bounding box.

Extract individual cell images (micro-patterns):

Cell snapshot is extracted and normalized against a reference image chromacity profile (one profile per stain combinations).

Normalization step includes the following steps

Deconvolution of main staining chromacity channels for cell snapshot.

Deconvolution of reference profile staining chromacity channels.

Robust z-scoring of each channel from the cell snapshot with regard to the reference profile Merging of normalized deconvolved channels into one cell-snapshot image and save in a physical file locally for further processing.

Merging of normalized deconvolved channels into one nuclei snapshot image after removing the bounding box around.

Save nuclei snapshot in local physical file.

Extract adjacent cell tissue area (macro-patterns):

For each cell image in the previous steps the FOV (image tile) from where it is extracted is normalized following steps of normalization related to micro-patterns.

After normalization FOV image is saved in physical local file.

Phase-4

Train model on micro pattern ballooned hepatocyte:

An experienced user manually selects a set of cell snapshot images representing normal hepatocytes and ballooned hepatocytes.

A deep learning model previously trained on ImageNet data set, is adapted with the set of cell snapshot images previously defined.

Using gradient descent an experience user defines optimal deep-learning configuration for ballooned cell snapshot pattern recognition.

Train model on micro pattern inflammatory cells:

Repeat steps of training for inflammatory cells and normal hepatocyte cell nuclei snapshot.

Train model on macro pattern NASH fibrosis:

An experienced user manually selects a set of cell FOV images from fibrosis stained WSI image representing normal FOVs (no collagen).

Peri-sinousoidal FOVs (collagen branching around sinousoids)

Pen-portal FOVs (collagen branching around portal areas)

Portal FOVs (collagen present in portal areas)

Bridging FOVs (collagen present in the form of bridges between main vascular structures portal areas and central vein).

A deep learning model previously trained on ImageNet data set, is adapted with the set of FOVs images previously defined.

Using gradient descent an experience user defines optimal deep-learning configuration NASH fibrosis pattern recognition.

Train model on macro pattern Hepatic fibrosis:

An experienced user manually selects a set of cell FOV images from fibrosis stained WSI image representing normal FOVs (no collagen).

Peri-sinousoidal FOVs (collagen branching around sinousoids)

Pen-portal FOVs (collagen branching around portal areas)

Portal FOVs (collagen present in portal areas)

Bridging FOVs (collagen present in the form of bridges between main vascular structures portal areas and central vein).

Deconvolution is applied on the previously defined data set to separate fibrosis staining from any other additional staining.

To characterize the morphological properties of each FOVs type defined in FOV images selected by an experienced user, fractal analysis is applied Fractal analysis is applied on the fibrosis deconvolved channel using "dragon curve" as a base pattern.

Statistical analysis is performed in each subset of FOVs as defined in FOV images selected by an experienced user, to measure mean, median, min, max, standard deviation.

Thresholds defining the classification boundaries of each FOVs based on the fractal index is defined as mean +/−1-2 X Std Apply models on typical WSI image:

Extract micro and macro patterns: Proceed as defined in Phase 3 for image extraction and normalization Ballooning Apply model on all cell-snapshots and compute class probability and predicted class label (highest probability label)

Ballooning score cell count for WSI is defined number of ballooned cells with predicted label "Ballooned Cell" and prediction probability>95%.

Ballooning score cell proportion for WSI is defined as the ratio of number of ballooned cells with total number of cells.

Inflammation

Use method from Rexhepaj et al (Eur Respir J. 2015 Dec;46(6):1762-72) to randomize FOVs only from the biopsy part of the WSI Filter out FOVs with big vascular structures Experienced user selects first 10 FOVs Apply model on all cell-snapshots from FOVs above and compute class probability and predicted class label (highest probability label)

Inflammation score cell count for WSI is defined number of inflammatory cells with predicted label "Inflammation Cell" and prediction probability>95%.

Inflammation score as defined by Kleiner et al (2005) is defined manually by an experienced user on 10 FOVs above NASH fibrosis Apply model defined in train model on macro pattern NASH fibrosis in all pre-normalized FOVs Define a NASH fibrosis score based on guidelines from Kleiner et al (2005).

Hepatic fibrosis

Apply model defined in train model on macro pattern Hepatic fibrosis in all pre-normalized FOVs Define a Hepatic fibrosis score as A mean fractal index over all FOVs.

A mean fractal index over all FOVs excluding FOVs predicted as portal area.

A mean fractal index is defined per category of FOV

According to a further aspect, the present invention also relates to complete automatization and/or digitalization including steatosis pattern recognition and scoring. Steatosis score may be determined by classical method or pattern recognition and scoring using DL method.

Lastly, the invention provides innovative functionalities of computational pathology pipeline which are:

1) Pattern recognition

Steatosis:

Algorithm to filter false positive regions (white space looking alike lipid vacuoles but belong to vascular structures) that are morphologically similar to lipid vacuoles.

Algorithm to selectively filter out white areas that are not morphologically similar to lipid vacuoles (too small or big enough but not corresponding to pre-defined morphological properties).

Semi-automated companion method to help human annotator at providing more robust estimation of underlying steatosis.

Inflammation

A novel pattern recognition approach and a model to differentiate between inflammatory cell nuclei and normal hepatocyte nuclei.

A novel pattern recognition approach and a model to recognize portal regions areas from a digitalized biopsy image.

An approach to translate cell-based predictions into clinical inflammatory scores.

Ballooning

A novel pattern recognition approach and a model to differentiate between ballooned nuclei and normal hepatocytes based on a pattern recognition model and morphological criteria of balloon hepatocytes.

Fibrosis

A novel pattern recognition approach and a model to differentiate main fibrosis patterns in biopsy sections.

A novel approach to filter out regions of the slide in order to avoid biais from non-pathological collagen-positive areas.

A novel approach to increase granularity of fibrosis score 3 and 4 for sub-group analysis, using septa analysis 2) Data management and analysis Based on prior histopathological and analytical knowledge, the authors have defined mathematical models to represent key patterns and cell-type.

models of potential artefacts during experimentation leading to data that could be miss-interpreted a new approach developed and integrated to the workflow to address staining variability and facilitate the generalization of all pattern recognition models above.

Most of the work above is based on prior art adapted/modified based on prior data analytical and histopathological domain knowledge.

All prior methods are covered by licenses allowing full exploitation and commercialization.

In some embodiments, thanks to the methods of the invention, a decision may be taken to give life style recommendations to a subject, or to administer at least one NAFLD, NASH or liver fibrosis therapy. Such a classification of a subject as a receiver or TBT patient is based on DL models application and scoring of hepatocyte ballooning, lobular inflammation and fibrosis compared with (NTBT).

The invention thus further relates to anti-NAFLD, anti-NASH or anti-fibrotic compound for use in a method for treating NAFLD, NASH or liver fibrosis in a subject in need thereof, wherein the subject has been identified thanks to a method according to the invention.

Illustrative anti-NASH and anti-fibrotic compounds are listed below:

a compound of formula (I):

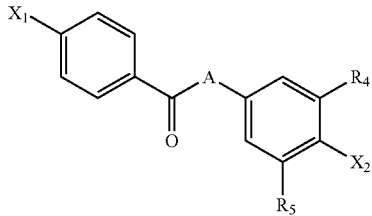

wherein:

X1 represents a halogen, a R1, or G1-R1 group;

A represents a CH=CH or a CH2-CH2 group;

X2 represents a G2-R2 group;

G1 and G2, identical or different, represent an atom of oxygen or sulfur;

R1 represents a hydrogen atom, an unsubstituted alkyl group, an aryl group or an alkyl group that is substituted by one or more halogen atoms, an alkoxy or an alkylthio group, cycloalkyl groups, cycloalkylthio groups or heterocyclic groups;

R2 represents an alkyl group substituted by at least a —COOR3 group, wherein R3 represents a hydrogen atom, or an alkyl group that is substituted or not by one or more halogen atoms, cycloalkyl groups, or heterocyclic groups.

R4 and R5, identical or different, representing an alkyl group that is substituted or not by one or more halogen atoms, cycloalkyl groups, heterocyclic groups;

or a pharmaceutically acceptable salt thereof;

Acetyl-CoA carboxylase inhibitors like GS-0976, ND-654, AC-8632, and PF05175157.

Anti-LPS antibodies like IMM-124-E

Apical sodium-codependent bile acid transporter inhibitors like A-4250, volixibat, maralixibat formely SHP-625, GSK-2330672, elobixibat, and CJ-14199.

bioactive lipids like 5-hydroxyeicosapentaenoic acid (15-HEPE, DS-102), arachidonic acid, eicosapentaenoic acid, and docosahexaenoic acid.

Cannabinoid CB1 receptor antagonists like GRC-10801, MRI-1569, MRI-1867, DBPR-211, AM-6527 ; AM-6545, NESS-11-SM, CXB-029, GCC-2680, TM-38837, Org-50189, PF-514273, BMS-812204, ZYO-1, AZD-2207, AZD-1175, otenanabant, ibipinabant, surinabant, rimonabant, drinabant, SLV-326, V-24343, and 0-2093.

Caspase inhibitors like emricasan, belnacasan, nivocasan, IDN-7314, F-573, VX-166, YJP-60107, MX-1122, IDN-6734, TLC-144, SB-234470, IDN-1965, VX-799, SDZ-220-976, and L-709049.

Cathepsin inhibitors like VBY-376, VBY-825, VBY-036, VBY-129, VBY-285, Org-219517, LY3000328, RG-7236, and BF/PC-18.

CCR antagonists like cenicriviroc (CCR2/5 antagonist); PG-092, RAP-310, INCB-10820, RAP-103, PF-04634817, and CCX-872.

Diacylglycerol-O-acyltransferase (DGAT) inhibitors like IONIS-DGAT2Rx formely ISIS-DGAT2Rx, LY-3202328, BH-03004, KR-69530, OT-13540, AZD-7687, and ABT-046.

Dipeptidyl peptidase IV (DPP4) inhibitors like evogliptin, vidagliptin, fotagliptin, alogliptin, saxagliptin, tilogliptin, anagliptin, sitagliptin, retagliptin, melogliptin, gosogliptin, trelagliptin, teneligliptin, dutogliptin, linagliptin, gemigliptin, yogliptin, betagliptin, imigliptin, omarigliptin, vidagliptin, and denagliptin.

Dual NOX (NADPH oxidase) 1&4 inhibitors like GKT-831 (2-(2-chlorophenyl)-4-[3-(dimethylamino) phenyl]-5-methyl-1H-pyrazolo[4,3-c]pyridine-3,6(2H,5H)-dione) formely GKT137831, and GKT-901.

Extracellular matrix protein modulators like CNX-024, CNX-025, and SB-030.

Fatty acid synthase inhibitors like TVB-2640, TVB-3664, TVB-3166, TVB-3150, TVB-3199, TVB-3693; BZL-101, 2-octadecynoic acid, MDX-2, Fasnall , MT-061, G28UCM, MG-28, HS-160, GSK-2194069, KD-023, and cilostazol.

Stearoyl CoA desaturase-1 inhibitors/fatty acid bile acid conjugates (FABAC);

Farnesoid X receptor (FXR) agonists like obeticholic acid, GS-9674, LJN-452, and EDP-305, AKN-083, INT-767, GNF-5120, LY2562175, INV-33, NTX-023-1, EP-024297, Px-103, and SR-45023.

Fibroblast Growth Factor 19 (FGF-19) recombinants like NGM-282

Fibroblast Growth Factor 21 (FGF-21) agonists like PEG-FGF21 formely BMS-986036, YH-25348, BMS-986171, YH-25723, LY-3025876, and NNC-0194-0499.

Galectin 3 inhibitors like GR-MD-02, TD-139, ANG-4021, Galectin-3C, LJPC-201, TFD-100, GR-MD-03, GR-MD-04, GM-MD-01, GM-CT-01, GM-CT-02, Gal-100, and Gal-200.

Glucagon-like peptide-1 (GLP-1) analogs like semaglutide, liraglutide, exenatide, albiglutide, dulaglutide, lixisenatide, loxenatide, efpeglenatide, taspoglutide, MKC-253, DLP-205, and ORMD-0901.

GLP-1 receptor agonists

G-protein coupled receptor (GPCR) modulators like CNX-023.

Integrin inhibitors; integrin inhibitors of Pliant Therapeutic like integrin inhibitors of Indalo Therapeutics, integrin inhibitors of St Louis University, ProAgio, and GSK-3008348.

Leukotriene (LT)/Phosphodiesterase (PDE)/Lipoxygenase (LO) inhibitors like tipelukast (formely MN-001), tomelukast, sulukast, masilukast, zafirlukast, pranlukast, montelukast, gemilukast, verlukast, aklukast, pobilikast, cinalukast, and iralukast.

Macrolides like solithromycin, azithromycin, and erythromycin.

miRNA antagonists like RG-125 formely AZD4076, RGLS-5040, RG-101, MGN-5804, and MRG-201.

MMP9 stimulator like MMP9 stimulator of Elastomic Ab

Monoclonal antibodies like bertilimumab, NGM-313, IL-20 targeting mAbs, fresolimumab (antiTGFβ) formely GC1008, timolumab formely BTT-1023, namacizumab, omalizumab, ranibizumab, bevacizumab, lebrikizumab, epratuzumab, felvizumab, matuzumab, monalizumab, reslizumab, inebilizumab, foralumab (NI-0401, anti-CD3), simtizumab (GS-6624) mAb against LOXL2, and ustekinumab an anti-TNF antibody.

mTOR modulators like MSDC-0602, AAV gene therapy co-administered with SVP-sirolimus.

nuclear receptor ligands like DUR-928 formely DV 928.

P2Y13 protein agonists like CER-209

Protease-activated receptor (PAR)-2 antagonists like PZ-235, and NP-003.

Protein kinase modulators like CNX-014, MB-11055, ALF-1, mangiferin, amlexanox, GS-444217, REG-101, and valine.

PPAR alpha agonists like fenofibrate, ciprofibrate, pemafibrate, gemfibrozil, clofibrate, binifibrate, clinofibrate, clofibric acid, nicofibrate, pirifibrate, plafibride, ronifibrate, theofibrate, tocofibrate, and SR10171;

PPAR gamma agonists like Pioglitazone, deuterated pioglitazone, Rosiglitazone, efatutazone, ATx08-001, OMS-405, CHS-131, THR-0921, SER-150-DN, KDT-501, GED-0507-34-Levo, CLC-3001, and ALL-4.

PPAR delta agonists like GW501516 (Endurabol or ({4-[({4-methyl-2-[4-(trifluoromethyl) phenyl]-1,3-thiazol-5-yl}methyl)sulfanyl]-2-methylphenox}acetic acid)) or MBX8025 (Seladelpar or {2-methyl-4-[5-methyl-2-(4-trifluoromethyl-phenyl)-2H-[1,2,3]triazol-4-ylmethylsylfanyl]-phenoxy}-acetic acid) or GW0742 ([4-[[[2-[3-fluoro-4-(trifluoromethyl) phenyl]-4-methyl-5-thiazolyl]methyl]thio]-2-methyl phenoxy] acetic acid) or L165041 or HPP-593 or NCP-1046.

PPARalpha/gamma agonists like Saroglitazar, Aleglitazar, Muraglitazar, Tesaglitazar, and DSP-8658.

PPARalpha/delta agonists likeElafibranor, T913659.

PPAR gamma/delta like conjugated linoleic acid (CLA) like T3D-959.

PPAR alpha/gamma/delta agonists or PPARpan agonists like IVA337 or TTA (tetradecylthioacetic acid) or Bavachinin or GW4148 or GW9135, or Bezafibrate or Lobeglitazone, or CS038.

Rho-associated protein kinase 2 (ROCK2) inhibitors like KD-025, TRX-101, BA-1049, LYC-53976, INS-117548, and RKI-1447.

signal-regulating kinase 1 (ASK1) inhibitors like GS-4997

Sodium-glucose transport (SGLT) 2 inhibitors like remogliflozin, dapagliflozin, empagliflozin, ertugliflozin, sotagliflozin, ipragliflozin, tianagliflozin, canagliflozin, tofogliflozin, janagliflozin, bexagliflozin, luseogliflozin, sergliflozin, HEC-44616, AST-1935, and PLD-101.

stearoyl CoA desaturase-1 inhibitors/fatty acid bile acid conjugates like aramchol, GRC-9332, steamchol, TSN-2998, GSK-1940029, and XEN-801.

thyroid hormone receptor β (THR β) agonists like VK-2809, MGL-3196, MGL-3745, SKL-14763, sobetirome, BCT-304, ZYT-1, MB-07811, and eprotirome.

Toll Like Receptor 2 and 4 (TLR-2 and 4) antagonists like naltrexone, JKB-121, M-62812, resatorvid, dendrophilin, CS-4771, AyuV-1, AyuV-25, NI-0101, EDA-HPVE7, and eritoran.

Tyrosine kinase receptor (RTK) modulators; CNX-025, and KBP-7018

Vascular adhesion protein-1 (VAP-1) inhibitors like PXS-4728A, CP-664511, PRX-167700, ASP-8232, RTU-1096, RTU-007, and BTT-1023.

Vitamin D receptor (VDR) agonists like calciferol, alfacalcidol, 1,25-dihydroxyvitamin D3, Vitamin D2, Vitamin D3, calcitriol, Vitamin D4, Vitamin D5, dihydrotachysterol, calcipotriol; tacalcitol 1,24-dihydroxyvitamin D3, and paricalcitol.

Acetyl-CoA carboxylase inhibitors like GS-0976, ND-654, AC-8632, and PF05175157. Other acetyl-CoA carboxylase inhibitors like CP640186, gemcabene, and MK-4074.

Adenosine A3 receptor agonists like 2-(1-Hexynyl)-N-methyladenosine, Piclidenoson CF101 (IB-MECA), Namodenoson CF-102, 2-CI-IB-MECA, CP-532,903, Inosine, LUF-6000, and MRS-3558.

Aldosterone antagonists and mineralocorticoid receptor antagonists like Apararenone (MT 3995), Amiloride, Spironolactone, Eplerenone, Canrenone and potassium canrenoate, progesterone, drospirenone, gestodene, and benidipine.

AMP activated protein kinase stimulators like PXL-770, MB-11055 Debio-0930B metformin, CNX-012, 0-304, mangiferin calcium salt, eltrombopag, carotuximab, and Imeglimin.

Amylin receptor agonist and Calcitonin receptor agonists include, but are not limited to, KBP-042 and KBP-089.

Antisense oligonucleotide targeting transforming growth factor beta 2 include, but are not limited to ASPH-0047, IMC-TR1 and ISTH-0047.

Angiopoietin-related protein-3 inhibitors like ARO-ANG3, IONIS-ANGGPTL3-LRx or AKCEA-ANGPTL3LRx, evinacumab, and ALN-ANG.

Anti-LPS antibodies like IMM-124-E

Apical sodium-codependent bile acid transporter inhibitors like A-4250, volixibat, maralixibat formely SHP-625, GSK-2330672, elobixibat, and CJ-14199.

Betaine anhydrous or RM-003;

Bile acids like obeticholic acid (OCA) and UDCA, norursodeoxycholic acid, and ursodiol.

bioactive lipids like 5-hydroxyeicosapentaenoic acid (15-HEPE, DS-102)

Cannabinoid CB1 receptor antagonists like GRC-10801, MRI-1569, MRI-1867, DBPR-211, AM-6527 : AM-6545, NESS-11-SM, CXB-029, GCC-2680, TM-38837, Org-50189, PF-514273, BMS-812204, ZYO-1, AZD-2207, AZD-1175, otenabant, ibipinabant, surinabant, rimonabant, drinabant, SLV-326, V-24343, 0-2093.

Cannabinoid CB2 receptor mimetics like anabasum (Resunab, JKT-101).

Caspase inhibitors like emricasan, belnacasan, nivocasan, IDN-7314, F-573, VX-166, YJP-60107, MX-1122, IDN-6734, TLC-144, SB-234470, IDN-1965, VX-799, SDZ-220-976, L-709049.

Cathepsin inhibitors like VBY-376, VBY-825, VBY-036, VBY-129, VBY-285, Org-219517, LY3000328, RG-7236, BF/PC-18.

CCR antagonists like cenicriviroc (CCR2/5 antagonist) like PG-092, RAP-310, INCB-10820, RAP-103, PF-04634817, CCX-872.

CCR3 chemokine modulators and eotaxin 2 ligand inhibitors.

Diacylglycerol-O-acyltransferase (DGAT) inhibitors like IONIS-DGAT2Rx formely ISIS-DGAT2Rx, LY-3202328, BH-03004, KR-69530, OT-13540, AZD-7687, ABT-046.

Dipeptidyl peptidase IV (DPP4) inhibitors like evogliptin, vidagliptin, fotagliptin, alogliptin, saxagliptin, tilogliptin, anagliptin, sitagliptin, retagliptin, melogliptin, gosogliptin, trelagliptin, teneligliptin, dutogliptin, linagliptin, gemigliptin, yogliptin, betagliptin, imigliptin, omarigliptin, vidagliptin, denagliptin.

Dual NOX (NADPH oxidase) 1&4 inhibitors like GKT-831 formely GKT137831, GKT-901.

Extracellular matrix protein modulators; CNX-024, CNX-025, SB-030.

Stearoyl CoA desaturase-1 inhibitors/fatty acid bile acid conjugates (FABAC);

Farnesoid X receptor (FXR) agonists like obeticholic acid, GS-9674, LJN-452, EDP-305, AKN-083, INT- 767, GNF-5120, LY2562175, INV-33, NTX-023-1, EP-024297, Px-103, SR-45023.

Fatty acids like omega-3 fatty acids, Omacor or MF4637, fish oils, poly unsatured fatty acids (efamax, optiEPA).

Fatty Acid Synthase (FAS) inhibitors like TVB-2640; TVB-3199, TVB-3693BZL-101, 2-octadecynoic acid, MDX-2, Fasnall, MT-061, G28UCM, MG-28, HS-160, GSK-2194069, KD-023, and cilostazol.

Fibroblast Growth Factor 19 (FGF-19) receptor ligand or functional engineered variant of FGF-19

Fibroblast Growth Factor 19 (FGF-19) recombinants like NGM-282

Fibroblast Growth Factor 21 (FGF-21) agonists like PEG-FGF21 formely BMS-986036, YH-25348, BMS-986171, YH-25723, LY-3025876, NNC-0194-0499.

Galectin 3 inhibitors like GR-MD-02, TD-139, ANG-4021, Galectin-3C, LJPC-201, TFD-100, GR-MD-03, GR-MD-04, GM-MD-01, GM-CT-01, GM-CT-02, Gal-100, Gal-200.

Glucagon-like peptide-1 (GLP-1) analogs like semaglutide, liraglutide, exenatide, albiglutide, dulaglutide, lixisenatide, loxenatide, efpeglenatide, taspoglutide, MKC-253, DLP-205, ORMD-0901.

GLP-1 receptor agonists like LY-3305677, and Oxyntomodulin long acting.

G-protein coupled receptor (GPCR) modulators like CNX-023.

G-protein coupled receptor 84 antagonist (GPR84 antagonist), connective tissue growth factor ligand inhibitor and Free fatty acid receptor 1 agonist (FFAR1 agonist) like PBI-4050, PBI-4265, PBI-4283, and PBI-4299.

Growth hormone

Hedgehog cell-signalling pathway inhibitors like Vismodegib, TAK-441, IPI-926, Saridegib, Sonidegib/Erismodegib, BMS-833923/XL139, PF-04449913, Taladegib/LY2940680, ETS-2400, SHR-1539, and CUR61414.

Ileal sodium bile acid cotransporter inhibitors like A-4250, GSK-2330672, volixibat, CJ-15 14199, and elobixibat.

Immunomodulators like PBI-4050, PBI-4265, PBI-4283, PBI-4299 and AIC-649.

Insulin sensitizer and MCH receptor-1 antagonist like MSDC-0602 k, MSDC-0602, CSTI-100 and AMRI.

Integrin inhibitors like integrin inhibitors of Pliant Therapeutic, integrin inhibitors of Indalo Therapeutics, integrin inhibitors of St Louis University, ProAgio, GSK-3008348.

Ketohexokinase inhibitors like JNJ-28165722, JNJ-42065426; JNJ-42152981, JNJ-42740815, JNJ-42740828, and PF-06835919.

Leukotriene (LT)/Phosphodiesterase (PDE)/Lipoxygenase (LO) inhibitors like tipelukast (formely MN-001), tomelukast, sulukast, masilukast, zafirlukast, pranlukast, montelukast, gemilukast, verlukast, aklukast, pobilukast, cinalukast, iralukast.

Lysyl oxidase homolog 2 inhibitors like Rappaport, InterMune, Pharmaxis, AB-0023, Simtuzumab, PXS-5382A, and PXS-5338.

Macrolides; solithromycin, azithromycin, erythromycin.

miRNA antagonists like, RG-125 formely AZD4076, RGLS-5040, RG-101, MGN-5804, MRG-201.

Macrophage mannose receptor modulators like AB-0023, MT-1001, [18F]FB18mHSA, Xemys, technetium Tc 99 m tilmanocept, and CDX-1307.

Methyl CpG binding protein 2 modulator and transglutaminase inhibitors include, but are not limited to, cysteamine, EC Cysteamine, enteric-coated cysteamine bitartrate, cysteamine bitartrate (enteric-coated), Bennu, cysteamine bitartrate (enteric-coated), Raptor, cysteamine bitartrate, DR Cysteamine, delayed release enteric coated cysteamine bitartrate, mercaptamine, mercaptamine (enteric-coated), Bennu, mercaptamine (enteric-coated), Raptor, RP-103, RP-104, PROCYSBI, and mercaptamine (enteric-coated).

Metalloproteinase, MMP9 stimulator like MMP9 stimulator of Elastomic Ab

Mitochondrial carrier family inhibitor and Mitochondrial phosphate carrier protein inhibitor include, but are not limited to TRO-19622, Trophos, olesoxime, RG-6083, or RO-7090919.

Myeloperoxidase inhibitors include, but are not limited to PF-06667272

Monoclonal antibodies like bertilimumab, NGM-313, IL-20 targeting mAbs, fresolimumab (antiTGFβ) formely GC1008, timolumab formely BTT-1023, namacizumab, omalizumab, ranibizumab, bevacizumab, lebrikizumab, epratuzumab, felvizumab, matuzumab, monalizumab, reslizumab, inebilizumab.

mTOR modulators like MSDC-0602, AAV gene therapy co-administered with SVP-sirolimus.

NAD-dependent deacetylase sirtuin stimulator, PDE 5 inhibitor like NS-0200.

NF-kappa B inhibitors like LC-280126.

Nicotinic acid like Niacin or Vitamine B3

Nicotinic Acid Receptor (GPR109) Agonists like ARI-3037M0, MMF, LUF 6283, Acifran, IBC 293, MK-1903, GSK256073, MK-6892, MK-0354, SLx-4090, lomitapide, lexibulin, apabetalone, acifran, laropiprant, daporinad, anacetrapib, INCB-19602, ST-07-02, lomefloxacin, Niacin, and controlled release/ laropiprant, nitazoxanide (NTZ), its active metabolite tizoxanide (TZ) or other prodrugs of TZ such as RM-5061, non-steroid anti-inflammatory drugs (NSAIDs) include, but are not limited to F-351, salicylates (aspirin), acetaminophen, propionic acid derivatives (ibuprofen, naproxen), acetic acid derivatives (indomethacin, diclofenac), enolic acid derivatives (piroxicam, phenylbutazone), anthranilic acid derivatives (meclofenalmic acid, flufenamic acid), selective 25 COX-2 inhibitors (celecoxib, parecoxib), and sulfonanilides (nimesulide).

nuclear receptor ligands like DUR-928 formely DV 928.

P2Y13 protein agonists like CER-209

PDGFR modulators like BOT-501 and BOT-191.

Phenylalanine hydroxylase stimulators like Pegvaliase, sapropterin, AAV-PAH, CDX-6114, sepiapterin, RMN-168, ALTU-236, ETX-101, HepaStem, rolipram, and alprostadil Protease-activated receptor (PAR)-2 antagonists like PZ-235, NP-003.

Protein kinase modulators like CNX-014, MB-11055, ALF-1, mangiferin, amlexanox, GS-444217, REG-101, valine.

PPAR alpha agonists like fenofibrate, ciprofibrate, pemafibrate, gemfibrozil, clofibrate, binifibrate, clinofibrate, clofibric acid, nicofibrate, pirifibrate, plafibride, ronifibrate, theofibrate, tocofibrate, SR10171;

PPAR gamma agonists like Pioglitazone, deuterated pioglitazone, Rosiglitazone, efatutazone, ATx08-001, OMS-405, CHS-131, THR-0921, SER-150-DN, KDT-501, GED-0507-34-Levo, CLC-3001, ALL-4.

PPAR delta agonists like GW501516 (Endurabol or ({4-[({4-methyl-2-[4-(trifluoromethyl) phenyl]-1,3-thiazol-5-yl}methyl)sulfanyl]-2-methylphenoxy}acetic acid)) or MBX8025 (Seladelpar or {2-methyl-4-[5-methyl-2-(4-trifluoromethyl-phenyl)-2H-[I,2,3]triazol-4-ylmethylsylfanyl]-phenoxy}-acetic acid) or GW0742 ([4-[[[2-[4-3-fluoro-4-(trifluoromethyl) phenyl]-4-methyl-5-thiazolyl]methyl]thio]-2-methyl phenoxy] acetic acid) or L165041 or HPP-593 or NCP-1046.

PPARalpha/gamma agonists like Saroglitazar, Aleglitazar, Muraglitazar, Tesaglitazar, DSP-8658.

PPAR alpha/delta agonists like Elafibranor, T913659.

PPAR gamma/delta like conjugated linoleic acid (CLA), T3D-959.

PPAR alpha/gamma/delta agonists or PPARpan agonists like IVA337 or TTA (tetradecylthioacetic acid) or Bavachinin or GW4148 or GW9135, or Bezafibrate or Lobeglitazone, or CS038.

Rho-associated protein kinase 2 (ROCK2) inhibitors like KD-025, TRX-101, BA-1049, LYC-53976, INS-117548, RKI-1447.

signal-regulating kinase 1 (ASK1) inhibitors like GS-4997

Sodium-glucose transport (SGLT) 2 inhibitors like remogliflozin, dapagliflozin, empagliflozin, ertugliflozin, sotagliflozin, ipragliflozin, tianagliflozin, canagliflozin, tofogliflozin, janagliflozin, bexagliflozin, luseogliflozin, sergliflozin, HEC-44616, AST-1935, PLD-101.

stearoyl CoA desaturase-1 inhibitors/fatty acid bile acid conjugates like aramchol, GRC-9332, steamchol, TSN-2998, GSK-1940029, XEN-801.

thyroid receptor β (THR β) agonists like VK-2809, MGL-3196, MGL-3745, SKL-14763, sobetirome, BCT-304, ZYT-1, MB-07811, eprotirome.

Toll Like Receptor 4 (TLR-4) antagonists like naltrexone, JKB-121, M-62812, resatorvid, dendrophilin, CS-4771, AyuV-1, AyuV-25, NI-0101, EDA-HPVE7, eritoran.

Tyrosine kinase receptor (RTK) modulators like CNX-025, KBP-7018

Vascular adhesion protein-1 (VAP-1) inhibitors like PXS-4728A, CP-664511, PRX-167700, ASP-8232, RTU-1096, RTU-007, BTT-1023.

Vitamin D receptor (VDR) agonists like calciferol, alfacalcidol, 1,25-dihydroxyvitamin D3, Vitamin D2, Vitamin D3, calcitriol, Vitamin D4, Vitamin D5, dihydrotachysterol, calcipotriol; tacalcitol 1,24-dihydroxyvitamin D3, paricalcitol.

Vitamin E and isoforms, vitamin E combined with vitamin C and atorvastatin.

In a particular embodiment, the FAS inhibitor is a compound selected in the following list of compounds:

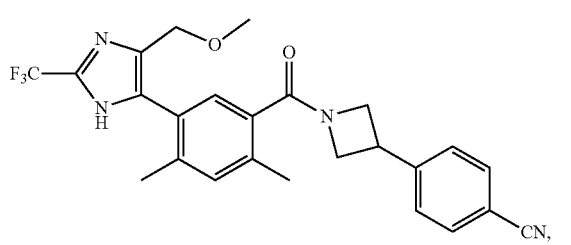

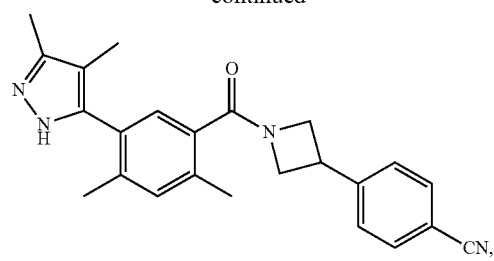

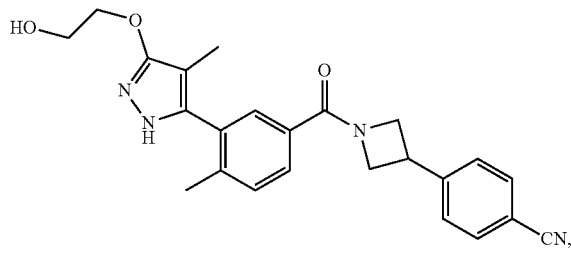

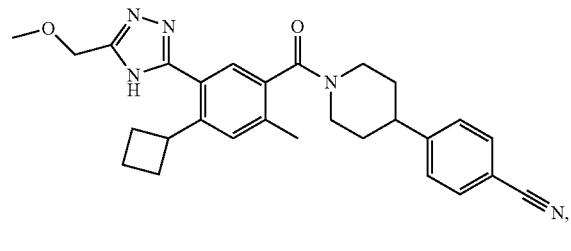

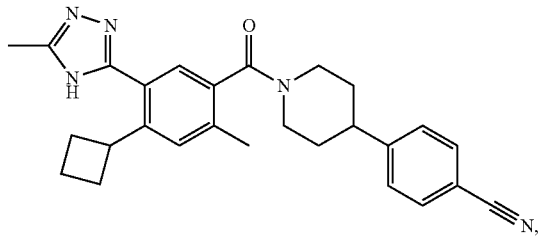

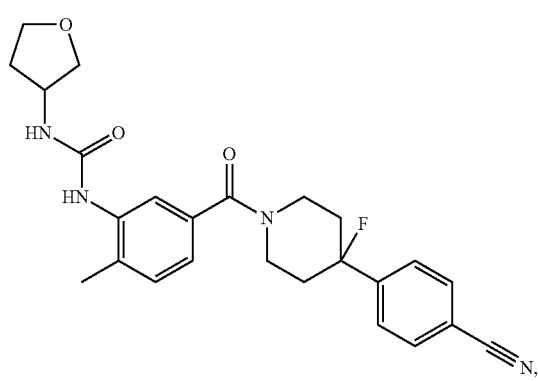

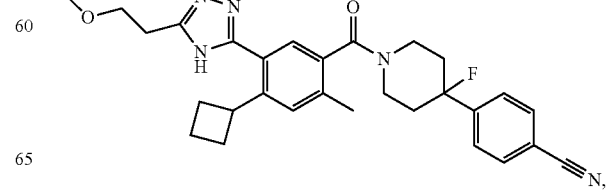

-continued

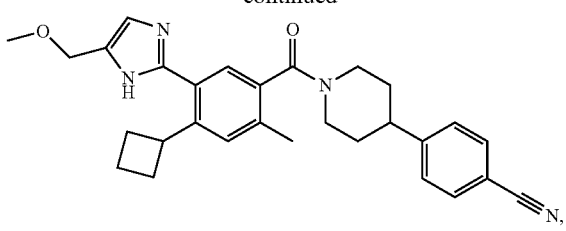

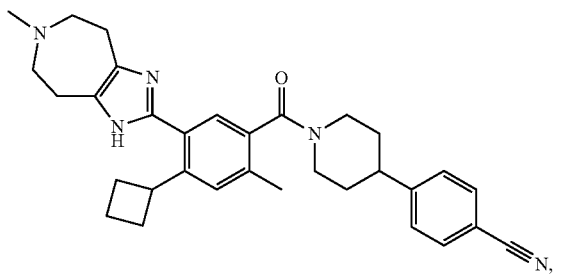

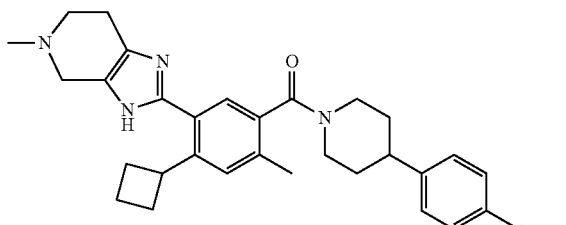

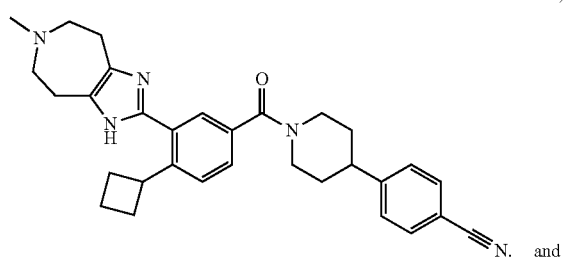

TVB-2640.

In another particular embodiment, the FAS inhibitor is selected from:

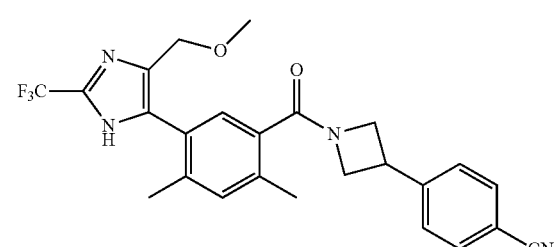

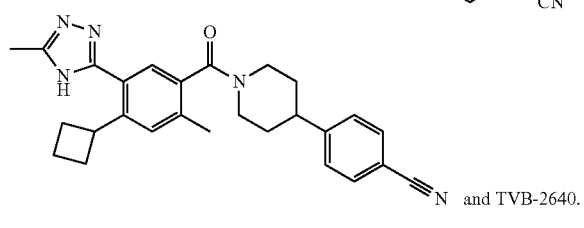

and TVB-2640.

In a particular embodiment, the FAS inhibitor is TVB-2640.

Other anti-NASH agents include KB-GE-001 and NGM-386 and NGM-395 and NC-10 and TCM-606F. Further anti-NASH agents include icosabutate, NC-101, NAIA-101 colesevelam, and PRC-4016.

Illustrative, non-limiting, anti-fibrotic agents useful in the practice of the present invention include:

Angiotensin II receptor blockers include but are not limited to Irbesartan;
antisense oligonucleotides targeting Transforming Growth Factor beta 2 (TGF-β2);
Bioactive lipids;
Caspase inhibitors;
Dual Farnesoid X receptor (FXR)/TGR5 agonists;
NOX (NADPH oxidase) inhibitors, such as Dual NOX (NADPH oxidase) 1&4 inhibitors;
Galectin 3 inhibitors;
Immunomodulators;
Integrin inhibitors;
Macrophage mannose receptor modulators;
Metalloprotease-9 (MMP-9) stimulators;
Monoclonal antibodies;
NF-kappa B inhibitors;
Non-Steroid Anti-Inflammatory Drugs (NSAIDs); and
PDGFR modulators.

Other anti-fibrotic agents include HEC-585, INV-240, RNAi therapeutic (e.g. Silence Therapeutics) and SAMiRNA program (Bioneer Corp).

Other illustrative antifibrotic agents include pirfenidone or receptor tyrosine kinase inhibitors (RTKIs) such as Nintedanib, Sorafenib and other RTKIs, or angiotensin II (AT1) receptor blockers, or CTGF inhibitor, or any antifibrotic compound susceptible to interfere with the TGFβ and BMP-activated pathways including activators of the latent TGFβ complex such as MMP2, MMP9, THBS1 or cell-surface integrins, TGFβ receptors type I (TGFBRI) or type II (TGFBRII) and their ligands such as TGFβ, Activin, inhibin, Nodal, anti-Müllerian hormone, GDFs or BMPs, auxiliary co-receptors (also known as type III receptors), or components of the SMAD-dependent canonical pathway including regulatory or inhibitory SMAD proteins, or members of the SMAD-independent or non-canonical pathways including various branches of MAPK signaling, TAK1, Rho-like GTPase signaling pathways, phosphatidylinositol-3 kinase/AKT pathways, TGFβ-induced EMT process, or canonical and non-canonical Hedgehog signaling pathways including Hh ligands or target genes, or any members of the WNT, or Notch pathways which are susceptible to influence TGFβ.

According to a particular embodiment, the anti-fibrotic agent is not an agent selected from: pirfenidone or receptor tyrosine kinase inhibitors (RTKIs) such as Nintedanib, Sorafenib and other RTKIs, or angiotensin II (AT1) receptor blockers, or CTGF inhibitor, or any antifibrotic compound susceptible to interfere with the TGFβ and BMP-activated pathways including activators of the latent TGFβ complex such as MMP2, MMP9, THBS1 or cell-surface integrins, TGFβ receptors type I (TGFBRI) or type II (TGFBRII) and their ligands such as TGFβ, Activin, inhibin, Nodal, anti-Müllerian hormone, GDFs or BMPs, auxiliary co-receptors (also known as type III receptors), or components of the SMAD-dependent canonical pathway including regulatory or inhibitory SMAD proteins, or members of the SMAD-independent or non-canonical pathways including various branches of MAPK signaling, TAK1, Rho-like GTPase signaling pathways, phosphatidylinositol-3 kinase/AKT pathways, TGFβ-induced EMT process, or canonical and non-canonical Hedgehog signaling pathways including Hh ligands or target genes, or any members of the WNT, or Notch pathways which are susceptible to influence TGFβ.

In a particular embodiment of the treatment of NASH or liver fibrosis comprises administering a compound of formula (I) selected in the group consisting of 1-[4-methylthiophenyl]-3-[3,5-dimethyl-4-carboxydimethylmethyloxy phenyl]prop-2-en-1-one, 1-[4-methylthiophenyl]-3-[3,5-dimethyl-4-isopropyloxy carbonyldimethylmethyloxyphenyl] prop-2-en-1-one, 1-[4-methylthiophenyl]-3-[3,5-dimethyl-4-tertbutyloxycarbonyldimethylmethyloxyphenyl] prop-2-en-1-one, 1-[4-trifluoromethylphenyl]-3-[3,5-dimethyl-4-tertbutyloxycarbonyl dimethylmethyloxyphenyl]prop-2-en-1-one, 1-[4-trifluoromethylphenyl]-3-[3,5-dimethyl-4-carboxydimethylmethyloxyphenyl]prop-2-en-1-one, 1-[4-trifluoromethyl oxyphenyl]-3-[3,5-dimethyl-4-tertbutyloxycarbonyldimethylmethyloxy phenyl] prop-2-en-1-one, 1-[4-trifluoromethyloxyphenyl]-3-[3,5-dimethyl-4-carboxydimethylmethyl oxyphenyl]prop-2-en-1-one, 2[2,6-dimethyl-4-[3-[4-(methylthio) phenyl]-3-oxo-propyl] phenoxy]-2-methyl-propanoic acid, and 2[2,6-dimethyl-4-[3-[4-(methylthio) phenyl]-3-oxo-propyl]phenoxy]-2-methyl-propanoic acid isopropyl ester; or a pharmaceutically acceptable salt thereof. In a further particular embodiment of the invention, the compound of formula (I) is 1-[4-methylthiophenyl]-3-[3,5-dimethyl-4-carboxydimethylmethyloxy phenyl]prop-2-en-1-one or a pharmaceutically acceptable salt thereof.

It is to be understood that the description above as well as the examples that follow are intended to illustrate and not limit the scope of the invention. Other aspects, advantages and modifications within the scope of the inventions will be apparent to those skilled in the art to which the invention pertains.

EXAMPLES

Materials and Methods

Preclinical Study design

Cell snapshots from biopsy samples stained with H&E selected out of a development cohort I (N=111), were used to train, test and validate the ballooning and inflammation prediction models.

For an independent validation of these models, we used a set of cell snapshots from cohort II (N=92) (FIG. 2).

In the training, testing and validating cohorts (III-V), animals were fed with a choline-deficient L-amino-acid-defined-diet that was supplemented with cholesterol (CDAA/chol diet) to induce fibrosis.

Cohort III (N=72) was used to train and calibrate the fibrosis stage prediction approach.

Cohorts IV (N=28) and V (N=105) were used for an independent validation (FIG. 2). In parallel, an expert user evaluated the NASH activity (i.e. inflammation and ballooned hepatocytes) and Kleiner fibrosis stage for all histological samples included in the study. One additional cohort (Cohort VI, N=79) was used for an independent validation of the inflammation quantification pipeline.

All inflammation, ballooning and fibrosis staging annotations were done by an expert histologist. For the ballooning parameter, an expert user digitally annotated (in all biopsy samples) all present ballooned and few adjacent normal hepatocytes.

Imaging

All digitalized slides were decomposed in tiles of 512×512 pixels using a data management pipeline developed in-house (FIG. 3). To score NASH activity, individual cell snapshots at 20× were selected from several sections to represent inflammatory cells and ballooned hepatocytes. An equal number of snapshots of normal hepatocytes was selected as negative control for each model (FIG. 4A). To score hepatic fibrosis, 510 fields of view (FOV) representing the main histological patterns of hepatic fibrosis were selected as a training set (FIG. 4B). A separate testing set of 173 FOVs was used to select the optimal model for further validation. Pathologically relevant FOVs (negative, peri-sinousoidal, peri-portal, bridging), as defined by the hepatic fibrosis DL model, are then selected for collagen morphometric measurements. An in-house (stain independent) algorithm was developed to normalize all histological images (at a given resolution) to a reference image. Following this normalization step, we applied the septa morphology measurement algorithm and CPA quantification on pathologically relevant FOVs (FIG. 4C). An expert annotator independently quantified (3DHistotech, QuantCenter) CPA levels on all samples of the training cohort after manually excluding important vascular regions.

After digitalization, digital glass slides were processed to extract high (20×0.5 μm) and low power magnification representations (4×2 μm). For the semi-automated quantification of fibrosis CPA an expert annotator manually excluded important vascular areas from each sample digital representation. Semi-automated intensity threshold separating collagen from staining background was manually adjusted prior to image analysis in order to achieve best possible quantification results (3DHistotech, QuantCenter). For each biopsy sample, after DL fibrosis staging pattern recognition to all FOVs, fully automated CPA and septa analysis pipeline were applied independently to quantify collagen morphology and total expression. DL prediction was used to filter-out non pathological FOVs. To be able to compare fully automated with manual scoring of inflammation, an ad-hoc step was added to the inflammation pipeline to:

a) Find the tissue region of WSI.
b) Find all FOVs equivalent to a 20× high power field under a microscope.
c) Automatically and randomly select 20 FOVs in the detected tissue area that do not also include an important portal region. In a second manual step, the expert annotator can select the first 10 FOVs conform the established scoring criteria (Kleiner, 2005, 41:1313-1321).
d) Using selected FOVs, DL inflammation model was applied to individual cell nuclei extracted at 20×.

An histologist scored the same FOVs manually as defined by the guidelines (Kleiner, 2005, 41:1313-1321) to compare against automated scoring.

Statistical learning

Convolutional Neural Networks (CNN) were used to construct individual models to detect inflammatory cells, ballooned hepatocytes and, a third model, to recognize histological patterns of NASH fibrosis. For all CNN, initial weights and architecture were adapted from a previous network (Szegedy, 2015) trained on the ImageNet dataset (Deng, 2009) FOV predictions were then transformed into a NASH Kleiner fibrosis stage to compare with equivalent pathologist score.

FOV predictions from the DL hepatic fibrosis scoring were transformed into a NASH Kleiner fibrosis score as defined in the guidelines (Kleiner, 2005, 41:1313-1321) to compare with equivalent pathologist score. CPA were reported at the biopsy level as ratio of total pathological collagen area to the total biopsy tissue area. Cohen's Kappa was used to quantify the agreement between manual and fully automated fibrosis scores on all available cohorts.

Results

Development of NASH Lobular Inflammation DL model

In a first learning iteration, a step-wise iteration of learning step was adopted (FIG. 5A). Several local minima of the loss function (i.e. negative likelihood) were identified and were explored. The most optimal network (best tradeoff between training-loss and validation-loss) was selected as the final model, showing an excellent accuracy (91%) for discriminating inflammatory cells from normal hepatocytes in independent dataset (Cohort I).

Development of NASH Hepatocyte Ballooning DL Model

A similar development approach to inflammation was used for this CNN model. Interestingly, a much better exploration of local minima in the second iteration was achieved (FIG. 5B) and show again excellent accuracy (98.2%) for discriminating ballooned cells from normal hepatocytes (Cohort I). Furthermore, in the independent dataset of 571 ballooned hepatocytes, 526 ballooned hepatocytes were accurately (92.1%) recognized (Cohort II).

Development of Hepatic Fibrosis DL Model

As for inflammation and ballooning models, the CNN parameter space was optimally explored. The final model showed excellent accuracy at recognizing all fibrosis patterns in the independent validation set (Cohort III): (a) collagen-negative regions (99.24% accuracy across 40 FOVs), (b) collagen-positive sinusoids (79% accuracy across 35 FOVs), (c) vascular regions (86% accuracy across 35 FOVs), (d) collagen-positive portal-triad (88% accuracy across 26 FOVs), (e) bridging fibrosis (92.24% accuracy across 37 FOVs).

Development of Hepatic Fibrosis morphometric Model

An initial evaluation of intra and inter-cohort variation of collagen intensity levels showed significant differences (FIG. 5C). This illustrates the possible impact for biasing collagen morphometric measurements and the need for a normalization step. Following the normalization step, comparison of semi-automated and fully-automated CPA measurements in the training cohort showed good correlation levels (FIG. 5D). Differences between the two sets of results are due to non-pathological areas and background staining removed by the fully automated approach.

Clinical validation of the fibrosis model

Analysis of variance for CPA levels across different fibrosis scores (Cohort V) showed a significant difference between F0 and F1 (p-value =0.006) or F2 (p-value =0.032) only visible on the fully automated CPA measurements (FIG. 6A-B). Morphology analysis of collagen septa (FIG. 6C) showed significant differences between the different types of FOVs (i.e. across all pathological FOVs). As morphological changes of collagen expression are expected with disease severity (fibrosis stage) these differences confirm the accuracy of DL predictions. Moreover, a good agreement was observed between the FOV DL pattern predictions transformed as Kleiner fibrosis stage (Kleiner, 2005, 41:1313-1321). and the fibrosis score determined manually by well-trained histologists (k=0.77 in the training set).

Validation of NASH Hepatocyte ballooning pattern recognition model

The most optimal balloon cell detection DL model (Accuracy=98%, cohort I) was selected to be applied at cellular level to all available biopsies on the validation cohort (Cohort II). Validation of the model at all annotated ballooned (N=422) and adjacent normal hepatocytes (N=149) was investigated. Results showed an excellent prediction accuracy (93.8%) on this cohort-independent set of cells (Table 1). An independent annotator reviewed falsely positively (FP) and negatively (FN) predicted cells to investigate the amount of mislabeled cell annotations (Table 1). Among the FN, the second reviewer deemed 21/23 cells to be ballooned hepatocytes.

TABLE 1

Contingency table derived from the comparison of NASH ballooning pipeline prediction and manual annotation on the validation cohort II. Numbers in bold are numbers of cells correctly predicted by the expert annotator and the automated pipeline. In italic are respectively the annotations of a second independent reviewer of false positive and false negative predictions.

|  |  | Predicted Hepatocyte Annotations | |
|---|---|---|---|
|  |  | Ballooned | Normal |
| Expert Hepatocyte Annotations | Ballooned | 399 | *23* (Small ballooned cells) n = 21 (Large ballooned cells) n = 2 |
|  | Normal | *12* | 137 |

Next step was application of the pipeline to full biopsies and comparison with manual annotations. As for the quantification of inflammation, ballooning model was applied to a subset of the validation cohort (N=19). We observed differences in term of ballooned cell count across scores and agreement between manual and automated ballooning scores

TABLE 2

Contingency table derived from the comparison of NASH ballooning pipeline scoring prediction and manual annotation on the validation cohort II for a representative set of samples. Numbers in bold are numbers of cells correctly predicted by the expert annotator and the automated pipeline.

|  |  | Predicted Ballooning Scores | | |
|---|---|---|---|---|
|  |  | HB = 0 | HB = 1 | HB = 2 |
| Expert Ballooning Scores | HB = 0 | 6 | 0 | 0 |
|  | HB = 1 | 2 | 8 | 0 |
|  | HB = 2 | 1 | 0 | 2 |

Validation of NASH automated hepatocyte lobular inflammation pipeline

Inflammatory pipeline was initially applied to 20 representative samples (Cohort VI) to validate the process of automated selection of 10 HPF for scoring of inflammation (FIG. 6). Comparison of mean number of foci between microscopy and WSI based scoring showed excellent correlation (R=0.907). Furthermore, there was a perfect agreement when #foci was transformed into a score (Kleiner, 2005, 41:1313-1321). These results showed the later method being suitable for large scale analysis of all remaining validation biopsies (Cohort VI) in a follow-up study.

Validation of inflammatory cell pattern recognition model

The most optimal inflammatory cell detection DL model (Accuracy=91%, cohort I) was selected to be applied to full cohort (Cohort I and VI).

Given the important number of cells per sample (~$10^6$) and in the interest of having complete data (i.e. whole biopsy), the analysis of inflammation was applied to a few samples (N=31) representing all inflammation scores (Cohort I). When looking at the distribution of total lobular inflammation, significant differences (p-value<0.001) between low and high scores were observed.

Clinical validation of the fibrosis pattern recognition model

The deep-learning algorithm showed excellent accuracy at predicting fibrosis histological patterns at FOV level (Accuracy=88%, cohort III). Moreover, a good agreement was observed between the FOV values transformed as Kleiner fibrosis stage (Kleiner, 2005, 41:1313-1321) and the fibrosis score determined manually by well-trained histologists (k=0.77 in the training set and k=0.93, k=0.70 in the validation studies) (Table 3).

automated activity scoring (but not only, fibrosis and steatosis pipelines are also integrated), use mapping of region of interests (e.g. steatosis vacuoles, inflammatory foci, balloon cells, collagen fibers) onto the digital representation of the tissue section as a scoring/diagnostic aid (FIG. 9).

In conclusion:

Deep learning paradigm can be used to generate models with excellent performances for automating NASH histological interpretation. Such automated interpretations are accurate both at the micro or macro cellular (FOV) level and biopsy level. Integration of a robust normalization step in all pipelines makes the quantification process scalable to new cohort without any modifications.

Scoring of ballooning can be fully automated with great accuracy and can also be used as a scoring companion (highlighting potential ballooned hepatocytes) ensuring no ballooned hepatocytes are missed.

For scoring of inflammation, a WSI-based approach could be an alternative to the microscopy-based approach. This approach may be combined with a DL inflammatory cell pattern recognition and foci count to fully automate the scoring process.

TABLE 3

Contingency table derived from the comparison of NASH fibrosis scores as defined by the expert histologist and as predicted by the automated fibrosis scoring pipeline. (From left to right) The left side of the table shows the results from the comparison in the training cohort, in the center we show the results from the 1$^{st}$ independent validation (Cohort IV) and in the right side are depicted results from the validation on a second (Cohort V) independent (Numbers in bold indicate the number of cases in which there is an agreement).

| | | Predicted scores Cohort III (Training) | | | | Predicted scores Cohort IV (Validation) | | | | Predicted scores Cohort V (Validation) | | | |
|---|---|---|---|---|---|---|---|---|---|---|---|---|---|
| | | F = 0 | F = 1 | F = 2 | F = 3 | F = 0 | F = 1 | F = 2 | F = 3 | F = 0 | F = 1 | F = 2 | F = 3 |
| Expert scores | F = 0 | 13 | 1 | 0 | 0 | 4 | 0 | 0 | 0 | 8 | 3 | 0 | 0 |
| | F = 1 | 6 | 11 | 5 | 1 | 0 | 2 | 0 | 0 | 4 | 9 | 2 | 0 |
| | F = 2 | 0 | 2 | 6 | 4 | 0 | 0 | 1 | 0 | 1 | 2 | 6 | 1 |
| | F = 3 | 0 | 0 | 2 | 21 | 0 | 1 | 0 | 22 | 0 | 5 | 10 | 54 |

Validation of NASH Fibrosis morphometric analysis pipeline

DL fibrosis pattern model was applied to all available biopsy sample FOVs (Cohort III-V). Upon fibrosis automated scoring prediction, these data were compared with manual fibrosis scores (Table 3). With regard to collagen expression the distribution of morphometric measurements across the different stages of fibrosis was investigated (Cohort V). As previously shown (Huang, 2013), there are significant differences in CPA mean levels between F0, F1&F2 and F3 (FIG. 7A). However, detected CPA levels in F1 and F2 remain similar due to non significant changes in the observed amount of collagen in the underlying biopsy sections. When the distribution of septa morphology analysis was investigated (FIG. 7B), this metric to better resolve the differences between F1 & F2 was observed (p-value=0.042).

Integration Into a Bioimage Analysis Software Such as Qupath.

QuPath provides the ability to develop plugins improving end's user experience of Artificial Intelligence (AI) algorithm within self-service applications (Bankhead et al, 2017). The authors illustrate how DL models can be integrated in an open-source computational pathology software (such as QuPAth) to increase user acceptance and experience (FIG. 8).

All the pipelines are integrated into the open-source platform QuPath, allowing users to review and validate Regarding the fibrosis model, after aggregation of the predictions at the biopsy level, the accuracy of predicted clinical scores was validated when compared to human expert annotations. Predictions of fibrosis FOV patterns are also of added value to CPA and septa quantification that can be specifically focused on pathologically relevant areas of the biopsy section. CPA and septa morphology can be used for a better discrimination of all fibrosis scores Although several methods have been proposed to automate quantification of collagen expression patterns (CPA, septa morphology) from biopsy images, no prior study has demonstrated the feasibility of automating the scoring of NASH fibrosis scores. We show how the process can be fully automated and furthermore, how the DL prediction information can be explored for focusing the quantification of collagen expression in pathologically relevant areas.

Finally, the state of the art linking the level of NASH activity to the risk of fibrosis evolution and linking fibrosis stage to risk of long term liver outcomes (cirrhosis, liver transplant, HCC or liver death), support the use of DL for evaluating the risk of fibrosis evolution to cirrhosis and for estimating the risk of long term serious complications.

Inflammation and ballooning pipelines were integrated into QuPath, providing to the user both the quantitative results as well as a qualitative mapping of interesting biological information (i.e. location of foci, location of balloon cells, location of steatosis . . . )

In comparison with manual annotations, DL-based scoring systems integrated in QuPath allow an exhaustive and reproducible analysis of all cells in a biopsy. For example, they give special attention to specific regions of cells more difficult to interpret by experts. These prediction scores may be used for high-throughput activity scoring in pre-clinical studies and in the future as companion diagnostic tools for clinical applications.

REFERENCES

Bankhead P, Loughrey MB, Fernandez JA, Dombrowski Y, McArt DG, Dunne PD, McQuaid S, Gray RT, Murray LJ, Coleman HG, James JA, Salto-Tellez M, Hamilton PW (2017) QuPath: Open source software for digital pathology image analysis. Sci Rep 7: 16878

Bedossa P (2014) Utility and appropriateness of the fatty liver inhibition of progression (FLIP) algorithm and steatosis, activity, and fibrosis (SAF) score in the evaluation of biopsies of nonalcoholic fatty liver disease. Hepatology 60: 565-575

Brunt EM, Janney CG, Di Bisceglie AM, Neuschwander-Tetri BA, Bacon BR (1999) Nonalcoholic steatohepatitis: a proposal for grading and staging the histological lesions. Am J Gastroenterol 94: 2467-2474

Deng J., Dong W., Socher R., Li L.-J., Li K., Fei-Fei L. (2009). Imagenet: a large-scale hierarchical image database, in IEEE Conference on Computer Vision and Pattern Recognition.

Kleiner DE, Brunt EM, Van Natta M, Behling C, Contos MJ, Cummings OW, Ferrell LD, Liu YC, Torbenson MS, Unalp-Arida A, Yeh M, McCullough AJ, Sanyal AJ (2005) Design and validation of a histological scoring system for nonalcoholic fatty liver disease. Hepatology 41: 1313-1321

Kleiner DE, Makhlouf HR (2016) Histology of Nonalcoholic Fatty Liver Disease and Nonalcoholic Steatohepatitis in Adults and Children. Clin Liver Dis 20: 293-312

LeCun Y, Bengio Y, Hinton G (2015) Deep learning. Nature 521: 436-444

Machado M, Marques-Vidal P, Cortez-Pinto H (2006) Hepatic histology in obese patients undergoing bariatric surgery. J Hepato/45: 600-606

Munteanu M, Tiniakos D, Anstee Q, Charlotte F, Marchesini G, Bugianesi E, Trauner M, Romero Gomez M, Oliveira C, Day C, Dufour JF, Bellentani S, Ngo Y, Traussnig S, Perazzo H, Deckmyn 0, Bedossa P, Ratziu V, Poynard T (2016) Diagnostic performance of FibroTest, SteatoTest and ActiTest in patients with NAFLD using the SAF score as histological reference. Aliment Pharmacol Ther 44: 877-889

O'Callaghan DS, Rexhepaj E, Gately K, Coate L, Delaney D, O'Donnell DM, Kay E, O'Connell F, Gallagher WM, O'Byrne KJ.(2015) Tumour islet Foxp3+ T-cell infiltration predicts poor outcome in nonsmall cell lung cancer. Eur Respir J. Dec;46(6):1762-72

Szegedy C, Liu W, Jia Y, Sermanet P, Reed S, Anguelov D, Erhan D, Vanhoucke V, Rabinovich A 2015 Going deeper with convolutions IEEE Conference on Computer Vision and Pattern Recognition (CVPR)

Younossi ZM, Gramlich T, Liu YC, Matteoni C, Petrelli M, Goldblum J, Rybicki L, McCullough AJ (1998) Nonalcoholic fatty liver disease: assessment of variability in pathologic interpretations. Mod Pathol 11: 560-565

The invention claimed is:

1. A method for determining and scoring hepatocyte lobular inflammation in a liver biopsy from a subject, the method comprising:
   providing a liver biopsy slide from said subject;
   using a deep learning model:
   determining a plurality of field of views (FOVs) on a digitized form off the liver biopsy slide; and
   selecting a subset of the plurality of FOVs and identifying inflammatory cell patterns within the subset of the plurality of FOVs;
   determining a hepatocyte lobular inflammation (LI) score for the liver biopsy slide based on the identified inflammatory cell patterns;
   wherein the LI score ranges from 0 to 3 and LI=0 corresponds to no inflammation, LI=1 corresponds to mild inflammation, LI=2 corresponds to moderate inflammation, and LI=3 corresponds to severe inflammation.

2. The method according to claim 1, wherein the deep learning model comprises a model trained based on training data obtained from liver biopsy imaging data comprising inflammatory cells and normal hepatocytes.

3. A method for diagnosing NASH in a subject, the method comprising:
   providing a liver biopsy slide from said subject;
   using a deep learning model:
   determining a plurality of field of views (FOVs) on a digitized form of the liver biopsy slide; and
   selecting a subset of the plurality of FOVs and identifying inflammatory cell patterns within the subset of the plurality of FOVs;
   identifying patterns of hepatocyte ballooning (HB) and score hepatocyte ballooning;
   determining a hepatocyte lobular inflammation (LI) score for the liver biopsy slide based on the identified inflammatory cell patterns;
   wherein the LI score ranges from 0 to 3 and LI=0 corresponds to no inflammation, LI=1 corresponds to mild inflammation, LI=2 corresponds to moderate inflammation, and LI=3 corresponds to severe inflammation; and
   wherein HB score ranges from 0 to 2 and HB=0 corresponds to no hepatocyte ballooning, HB=1 corresponds to moderate hepatocyte ballooning, and HB=2 corresponds to severe hepatocyte ballooning and wherein said HB score and said LI score are added to determine an Activity Index (AI), ranking from 0 to 5, wherein the subject is diagnosed as a NASH subject if AI≥2, with HB≥1 and LI≥1.

4. The method according to claim 3 wherein NASH is diagnosed when, the HB score is of at least 1, the LI score is of at least 1, and a steatosis score from the same subject is of at least 1.

5. A method for determining and scoring NASH fibrosis or liver fibrosis in a subject, the method comprising:
   providing a liver biopsy slide from said subject;
   using a deep learning model:
   determining a plurality of field of views (FOVs) on a digitized form of the liver biopsy slide;
   selecting a subset of the plurality of FOVs and identifying patterns of liver fibrosis and/or measuring collagen proportion area (CPA) within the subset of the plurality of FOVs;
   determining a liver fibrosis score for the liver biopsy slide based on the identified patterns and/or measured proportions;
   wherein the liver fibrosis (F) is scored as follows: F=0 corresponds to no liver fibrosis; F=1 corresponds to minimal liver fibrosis; F=2 corresponds to significant liver fibrosis; F=3 corresponds to moderate liver fibrosis; and F=4 corresponds to severe liver fibrosis.

6. The method according to claim 5, wherein the deep learning model comprises a model trained based on training data obtained from liver biopsy imaging data comprising normal and collagen-containing tissues.

7. The method according to claim 6, wherein the training data comprise data obtained from: normal field of views (FOVs) (no collagen); Peri-sinusoidal FOVs (collagen branching around sinusoids); Peri-portal FOVs (collagen branching around portal areas); Portal FOVs (collagen present in portal areas); and Bridging FOVs (collagen present in the form of bridges between main vascular structures portal areas and central vein).

8. A method for determining and scoring liver or hepatic steatosis in a subject, comprising:
   providing a liver biopsy slide from said subject;
   using a deep learning model:
     determining a plurality of field of views (FOVs) on a digitized form of the liver biopsy slide;
     selecting a subset of the plurality of FOVs and identifying patterns of hepatic steatosis or liver steatosis within the subset of the plurality of FOVs;
   determining a hepatic or liver steatosis (S) score based on the identified patterns of hepatic steatosis or liver steatosis, wherein the hepatic or liver steatosis (S) is scored as follows: S=0 corresponds to less than 5% steatosis, S=1 corresponds to 6%-33% steatosis; S=2 corresponds to 34%-66% steatosis, and S=3 corresponds to greater than 66% steatosis.

9. A non-transitory computer-readable storage medium comprising instructions which, when executed by a computer, cause the computer to carry out a method comprising:
   providing a liver biopsy slide from said subject;
   using a deep learning model:
     determining a plurality of field of views (FOVs) on a digitized form of the liver biopsy slide;
     selecting a subset of the plurality of FOVs, identifying patterns of hepatocyte ballooning and scoring the hepatocyte ballooning patterns;
   wherein hepatocyte ballooning (HB) score ranges from 0 to 2 and HB=0 corresponds to no hepatocyte ballooning HB=1 corresponds to moderate hepatocyte ballooning, and HB=2 corresponds to severe hepatocyte ballooning.

10. A non-transitory computer-readable storage medium comprising instructions which, when executed by a computer, cause the computer to carry out a method comprising:
   providing a liver biopsy slide from said subject;
   using a deep learning model:
     determining a plurality of field of views (FOVs) on a digitized form of the liver biopsy slide;
     selecting a subset of the plurality of FOVs and identifying patterns of hepatocyte lobular inflammation and scoring hepatocyte lobular inflammation from said liver biopsy slide; wherein lobular inflammation (LI) score ranges from 0 to 3 and LI=0 corresponds to no inflammation; LI=1 corresponds to mild inflammation; LI=2 corresponds to moderate inflammation, and LI=3 corresponds to severe inflammation; and
   identifying patterns of hepatocyte ballooning (HB) and scoring hepatocyte ballooning; wherein HB score ranges from 0 to 2 and HB=0 corresponds to no hepatocyte ballooning, HB=1 corresponds to moderate hepatocyte ballooning, and HB=2 corresponds to severe hepatocyte ballooning; and
   wherein said HB score and said LI score are added to determine an Activity Index (AI), ranking from 0 to 5, wherein the subject is diagnosed as a NASH subject if AI≥2, with HB≥1 and LI≥1.

* * * * *